United States Patent
Xu et al.

(10) Patent No.: US 10,513,510 B2
(45) Date of Patent: Dec. 24, 2019

(54) TOXIN AND METHOD FOR PREPARING INTERMEDIATE THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Jianyan Xu, Shanghai (CN); Ying Zhang, Shanghai (CN); Bolei Qu, Shanghai (CN); Guiyang Jiang, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 16/078,396

(22) PCT Filed: Feb. 24, 2017

(86) PCT No.: PCT/CN2017/074756
§ 371 (c)(1),
(2) Date: Aug. 21, 2018

(87) PCT Pub. No.: WO2017/144015
PCT Pub. Date: Aug. 31, 2017

(65) Prior Publication Data
US 2019/0055223 A1    Feb. 21, 2019

(30) Foreign Application Priority Data
Feb. 26, 2016 (CN) .......................... 2016 1 0107901

(51) Int. Cl.
*C07D 403/12* (2006.01)
*C07D 209/94* (2006.01)
*A61K 35/00* (2006.01)

(52) U.S. Cl.
CPC ......... *C07D 403/12* (2013.01); *C07D 209/94* (2013.01); *A61K 35/00* (2013.01); *Y02P 20/55* (2015.11)

(58) Field of Classification Search
CPC ............................ C07D 403/12; C07D 209/94
See application file for complete search history.

(56) References Cited

U.S. PATENT DOCUMENTS

| | | |
|---|---|---|
| 2010/0249190 A1 | 9/2010 | Lopez et al. |
| 2012/0003247 A1 | 1/2012 | Doronina et al. |

FOREIGN PATENT DOCUMENTS

| | | |
|---|---|---|
| CN | 1938046 A | 3/2007 |
| CN | 103826661 A | 5/2014 |

(Continued)

OTHER PUBLICATIONS

Pettit et al, "A Cobalt-Phosphine Complex Directed Reformatsky Approach to a Stereospecific Synthesis of the Dolastatin 10 Unit Dolaproine (Dap)1," Journal of Organic Chemistry, vol. 66, No. 25, pp. 8640-8642 (2001).

(Continued)

*Primary Examiner* — Joseph R Kosack
(74) *Attorney, Agent, or Firm* — Panitch Schwarze Belisario & Nadel LLP

(57) ABSTRACT

The present invention relates to a new toxin and a method for preparing an intermediate thereof. In particular, the present invention relates to a new toxin and a method for preparating intermediates of Formula (III) and Formula (IV) thereof, and a preparation method for synthesizing what is shown in general formula (I). The method comprises subjecting a chiral compound shown in general formula (III) to a series of protecting group additions, protecting group removal and amidation so as to obtain a compound as shown in general formula (I). The present method has the advantages of mild reaction conditions, simple operation, high optical purity and high synthetic yield, and thus is suitable for large-scale production.

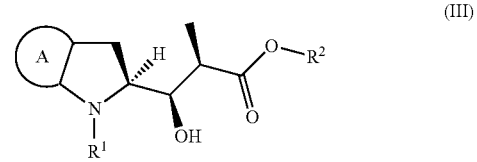

(III)

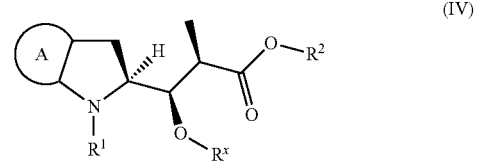

(IV)

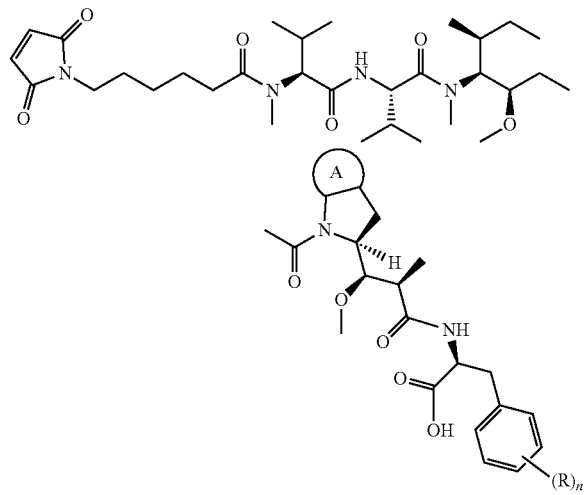

(I)

27 Claims, No Drawings

(56) References Cited

FOREIGN PATENT DOCUMENTS

| CN | 104254342 A | 12/2014 |
| WO | 2005/038392 A2 | 4/2005 |
| WO | 2008/081399 A2 | 7/2008 |
| WO | 2012143497 A2 | 10/2012 |
| WO | 2013/072813 A2 | 5/2013 |
| WO | 2013087716 A2 | 6/2013 |
| WO | 2016/127790 A1 | 8/2016 |

OTHER PUBLICATIONS

Pettit et al, "The Dolastatins; 18: Stereospecific Synthesis of Dolaproinel," Synthesis, pp. 719-725 (Jun. 1996).

Yasukawa et al, "Enzymatic Synthesis of Chiral Phenylalanine Derivatives by a Dynamic Kinetic Resolution of Corresponding Amide and Nitrile Substrates with a Multi-Enzyme System," Advanced Synthesis & Catalysis, vol. 354, No. 17, pp. 3327-3332 (2012).

Aïssa et al, "Total Syntheses of Amphidinolide T1, T3, T4, and T5," Journal of the American Chemical Society, vol. 125, No. 50, pp. 15512-15520 (2003).

Int'l Search Report dated Jun. 1, 2017 in Intl Application No. PCT/CN2017/074756.

TOXIN AND METHOD FOR PREPARING INTERMEDIATE THEREOF

CROSS-REFERENCE TO RELATED APPLICATION

This application is a section 371 of International Application No. PCT/CN2017/074756, filed Feb. 24, 2017, which was published in the Chinese language on Aug. 31, 2017, under International Publication No. WO 2017/144015 A, which claims priority under 35 u.s.c. § 119(b) to Chinese Application No. 201610107901.X, filed Feb. 26, 2016, the disclosures of which are incorporated herein by reference in their entirety.

FIELD OF THE INVENTION

The present invention relates to a new toxin and a method for preparing an intermediate thereof.

BACKGROUND OF THE INVENTION

The inventors disclose a novel type of ligand-cytotoxic drug conjugates in WO2016/127790. The ligand-cytotoxic drug conjugates and the pharmaceutical compositions comprising the same have good effects in the preparation of a medicament for treating cancer by receptor regulation. In the synthesis of such ligand-cytotoxic drug conjugates, the compound of formula (I) of the present invention is an important intermediate.

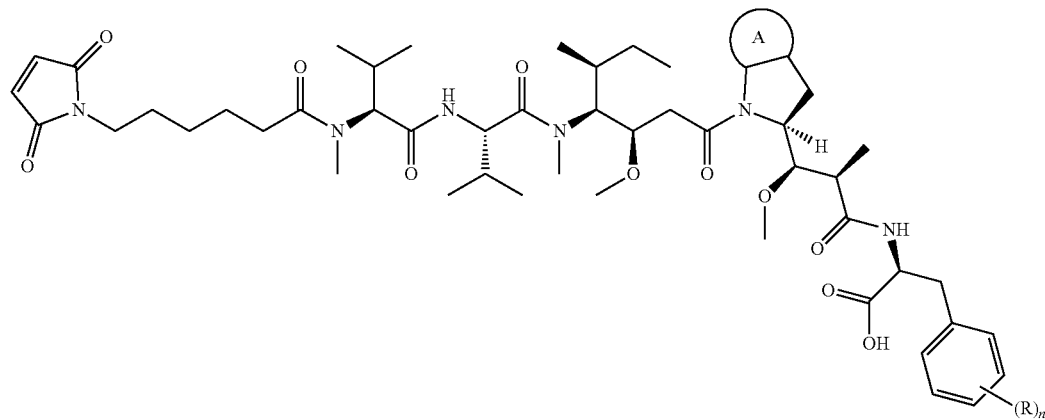

This intermediate has a similar structure to Mc-MMAF disclosed for the first time in the patent application WO2005/038392 by Seattle Genetics (U.S.A.), which discloses the synthetic of Mc-MMAF. However, in the synthetic route, there is no detailed disclosure of a specific preparation process for Fmoc-Dolaproine (Fmoc-Dap) and the starting materials. Fmoc-Dolaproine (Fmoc-Dap) has a similar chemical structure to the key intermediate of formula (IV), which is used synthesizing the compound of formula (I) of the present invention.

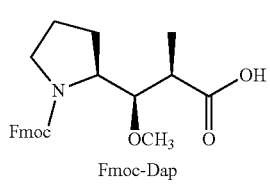

Fmoc-Dap

Therefore, the inventors identified related synthetic routes in the prior art of synthesizing Fmoc-Dolaproine (Fmoc-Dap). For example, George R. Pettit and Matthew P. Grealish reported a synthesis method of adding methyl directly in J. Org. Chem. 2001, 66, 8640-8642 (see Scheme 1), and a method of adding methyl after hydrolysis in Synthesis. 1996. 720 (see Scheme 2).

Scheme 1

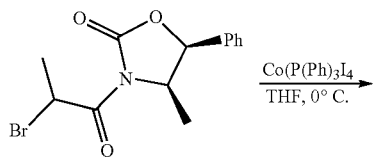

-continued

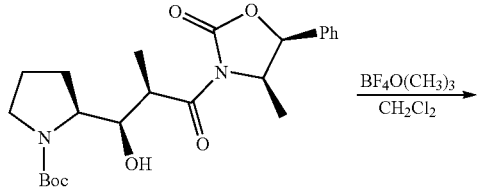

-continued

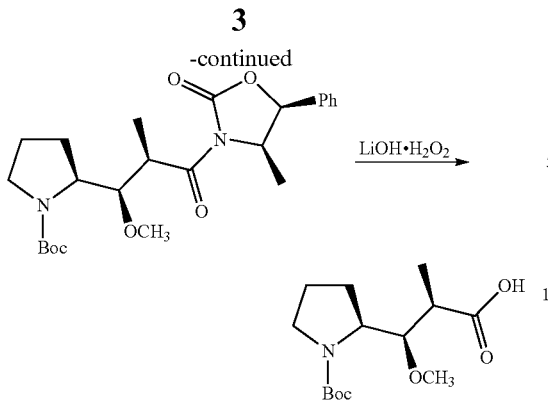

Scheme 2

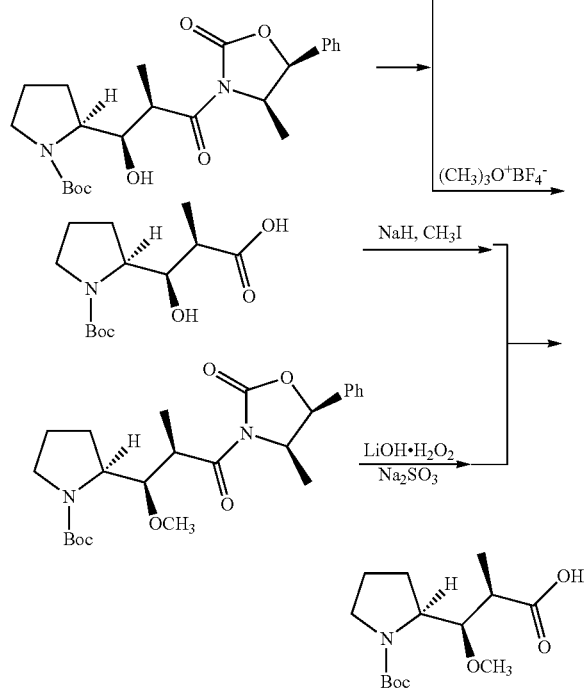

When synthesizing the fused ring substrate of formula (IV) of the present invention, the inventors used the above synthetic method of synthesizing Fmoc-Dolaproine (Fmoc-Dap), which a relatively high yield in the premise of original substrate. However, when the fused ring substrate of formula (IV) of the present invention was prepared, the yield of the target product was low and a amount of racemate was produced. Therefore, there are still a lot of difficulties and shortcomings in using the existing synthetic methods to synthesize the compound of formula (I) in a large scale. It is necessary to develop a method with a high yield that is suitable for the large-scale synthesis of the compound of formula (I).

BRIEF SUMMARY OF THE INVENTION

In view of the disadvantages of the synthetic process of the new toxin and its intermediate, the present invention provides a new route for synthesizing the compound of formula (I), which comprises subjecting a chiral compound of formula (III) to a series of protecting group additions, protecting group removal and amidation reactions to obtain the compound of formula (I). The method overcomes the limitations of the prior art on the substrate, has the advantages of mild reaction conditions, simple operation, high optical purity and high synthetic yield, and thus is suitable for large-scale production.

The present invention relates to a compound of formula (III),

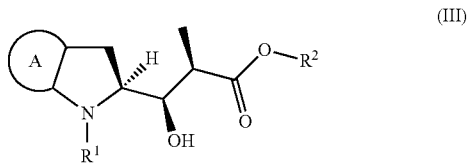

wherein:

A is a 3 to 8 membered ring, preferably a 3 membered ring;

$R^1$ is hydrogen or an amino protecting group, preferably Boc, Fmoc, Alloc, Troc, Teoc, CBz, Tosyl, Nosyl or t-Bu; and $R^2$ is hydrogen or a carboxyl protecting group, preferably DMB, Bn, Allyl, PfP, Me, PMB, MEM or t-Bu.

The present invention also relates to a method for preparing a compound of formula (III), characterized in that a chiral compound of formula (II) comprising a chiral auxiliary group ($R^3$) is hydrolyzed under an alkaline condition or optionally followed by addition of a carboxyl protecting group to obtain the compound of formula (III),

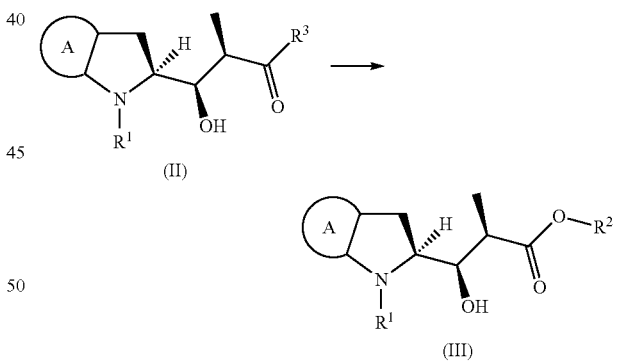

wherein:

the chiral auxiliary group ($R^3$) is selected from the group consisting of:

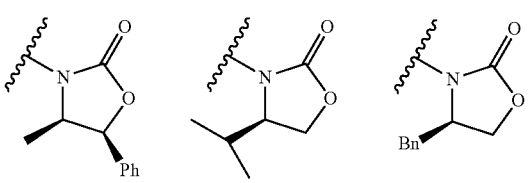

-continued

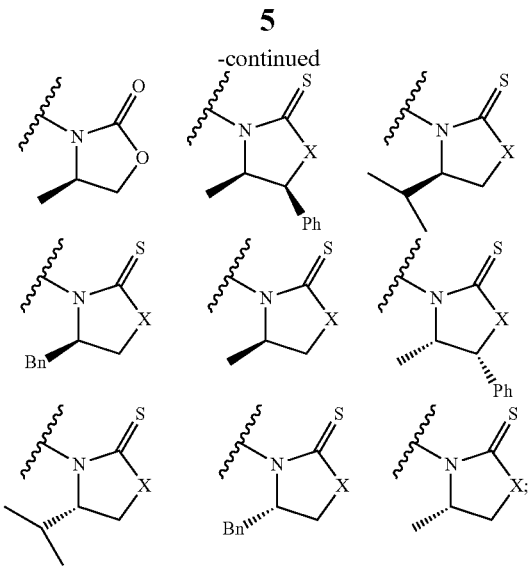

X is S or O;
the alkaline reagent is preferably sodium hydroxide, potassium hydroxide, sodium hydride, sodium carbonate, sodium bicarbonate, potassium carbonate, potassium bicarbonate, cesium carbonate or lithium hydroxide, and more preferably lithium hydroxide; and
$R^1$ to $R^2$ are as defined in formula (III).

The present invention also relates to a compound of formula (IV),

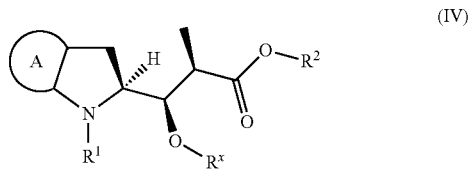

(IV)

wherein:
A is a 3 to 8 membered ring, preferably a 3 membered ring;
$R^1$ is hydrogen or an amino protecting group, preferably Boc, Fmoc, Alloc, Troc, CBz, Teoc, Tosyl, Nosyl or t-Bu;
$R^2$ is a carboxyl protecting group, preferably DMB, Bn, Allyl, PfP, Me, PMB, MEM or t-Bu; and
$R^x$ is selected from the group consisting of alkyl and cycloalkyl, wherein the alkyl and cycloalkyl are each independently and optionally substituted by one or more groups selected from the group consisting of alkyl, haloalkyl, halogen, hydroxy, amino, nitro, cyano, alkoxy, hydroxyalkyl, cycloalkyl, heterocyclyl, aryl, and heteroaryl; preferably methyl.

The present invention also relates to a process for preparing a compound of formula (IV), characterized in that a compound of formula (III) is reacted with an alkylating agent to obtain the compound of formula (IV),

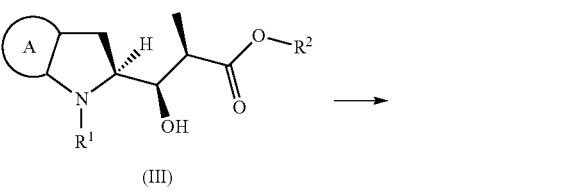

(III)

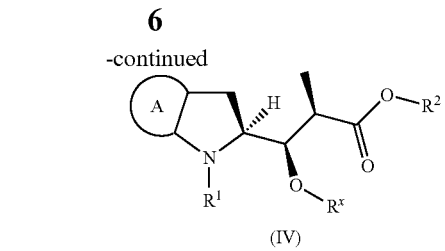

(IV)

wherein:
the alkylating agent is selected from the group consisting of alkyl halide, dimethyl sulfate, dimethyl carbonate, sulfonate, trimethyl phosphate and $Me_3^+BF_4^-$; preferably methyl iodide and $Me_3^+BF_4^-$; and
A, $R^1$, $R^2$ and $R^x$ are as defined in formula (IV).

The present invention also relates to a method for preparing a compound of formula (V) from a compound of formula (IV), wherein the carboxyl protecting group on the compound of formula (IV) is removed to obtain the compound of formula (V),

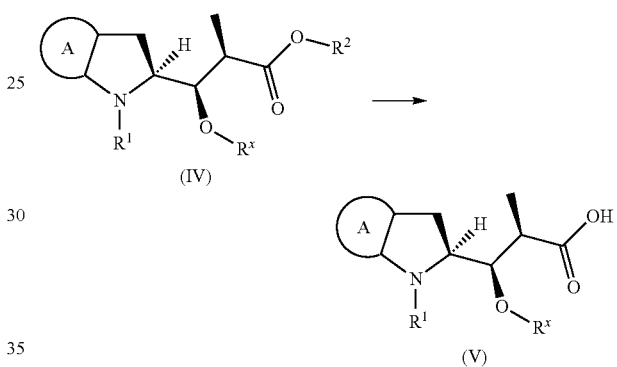

wherein:
A, $R^1$, $R^2$ and $R^x$ are as defined in formula (IV).

The present invention also relates to the process for preparing a compound of formula (V), characterized by further comprising a step of preparing a compound of formula (IV),

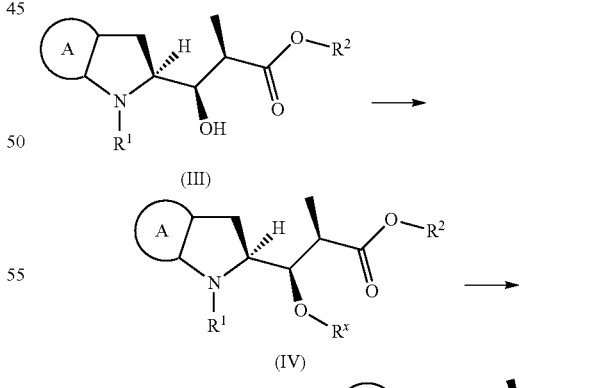

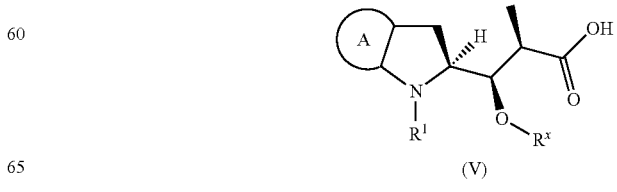

wherein:

A, $R^1$, $R^2$ and $R^x$ are as defined in formula (IV).

The present invention also relates to the process for preparing a compound of formula (V), characterized by further comprising a step of preparing a compound of formula (III),

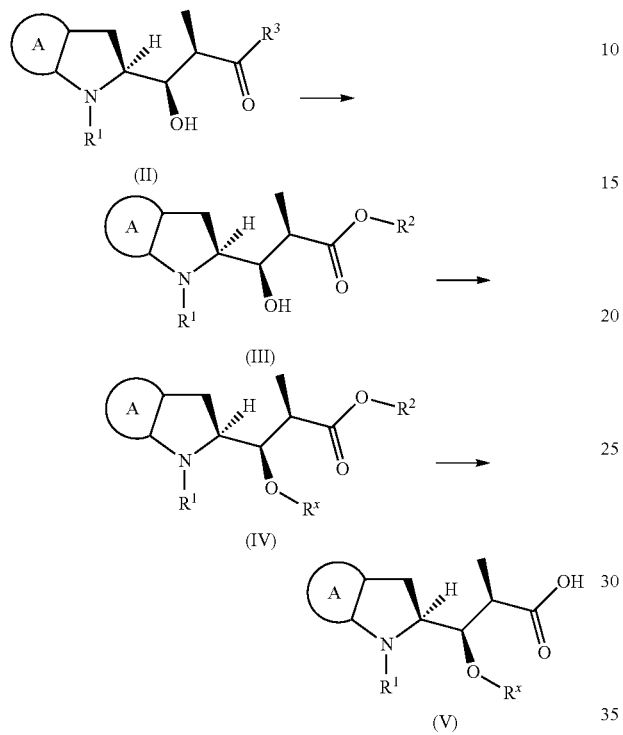

wherein:

A, $R^1$, $R^2$ and $R^x$ are as defined in formula (IV).

The present invention also relates to a process for preparing a compound of formula (I), compound of formula (III) with an alkylating agent to obtain a compound of formula (IV); removing the carboxyl protecting group on the compound of formula (IV) to obtain a compound of formula (V); and undergoing a series of reactions with the compound of formula (V) to obtain the compound of formula (I),

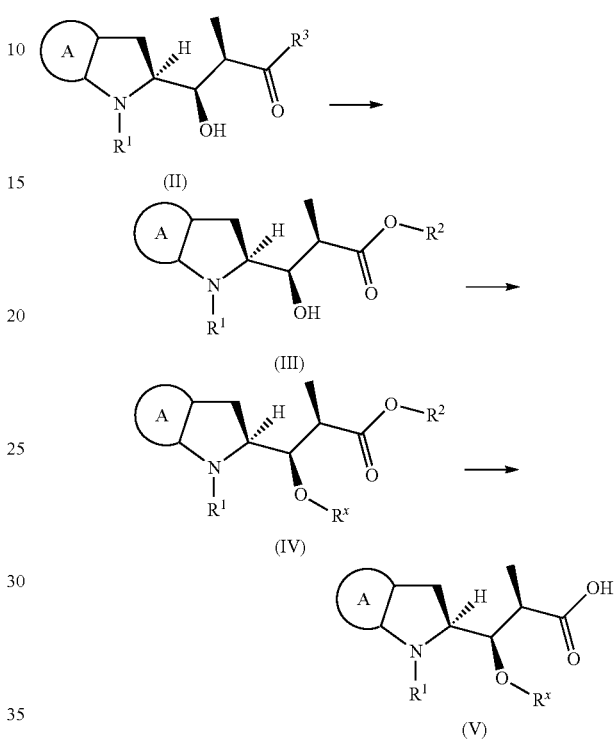

wherein:

A is a 3 to 8 membered ring, preferably a 3 membered ring;

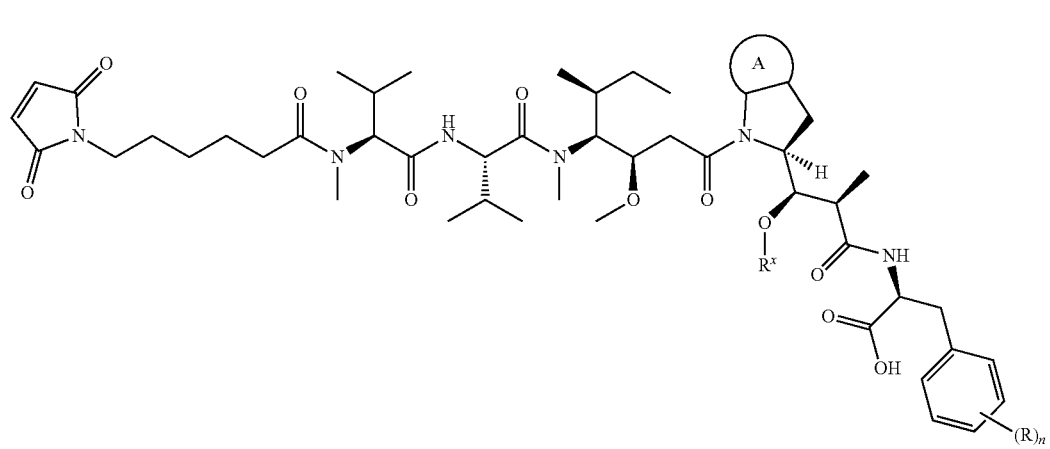

n is 1; 2; 3; 4 or 5;

characterized in that, the process comprises the steps of hydrolyzing a chiral compound of formula (II) comprising a chiral auxiliary group ($R^3$) under an alkaline condition or optionally followed by addition of a carboxyl protecting group to obtain a compound of formula (III); alkylating the R is halogen, preferably fluorine, chlorine, bromine or iodine, and most preferably fluorine;

$R^1$ is an amino protecting group, preferably Boc, Fmoc, Alloc, Troc, CBz, Teoc, Tosyl, Nosyl or t-Bu;

$R^2$ is a carboxyl protecting group, preferably DMB, Bn, Allyl, PfP, Me, PMB, MEM or t-Bu;

$R^x$ is selected from the group consisting of alkyl and cycloalkyl, wherein the alkyl and cycloalkyl are each independently and optionally substituted by one or more groups selected from the group consisting of alkyl, haloalkyl, halogen, hydroxy, amino, nitro, cyano, alkoxy, hydroxyalkyl, cycloalkyl, heterocyclyl, aryl, and heteroaryl; preferably $R^x$ is methyl; and n is 1, 2, 3, 4 or 5.

The present invention also relates to a process for preparing a compound of formula (I), characterized by further comprising a step of removing the amino protecting group on a compound of formula (V) to obtain a compound of formula (VI),

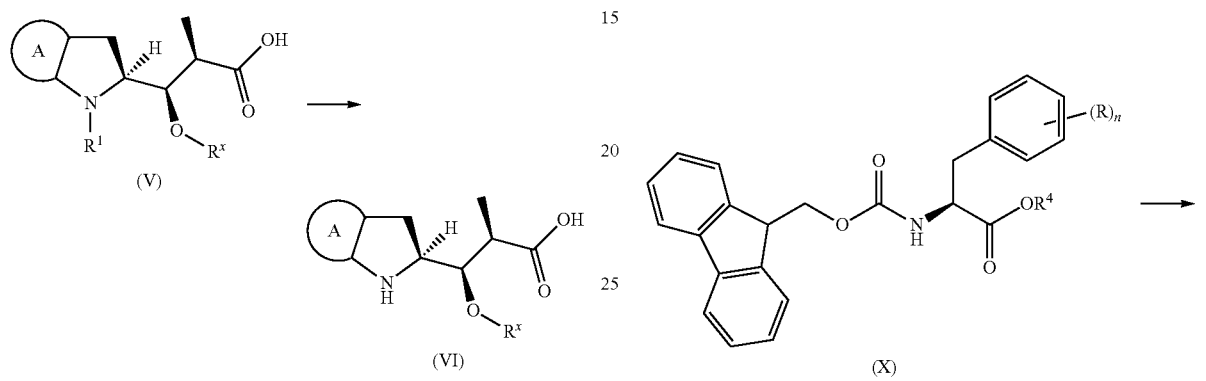

wherein:

A, $R^1$ and $R^x$ are as defined in formula (I).

The present invention also relates to a process for preparing a compound of formula (I), characterized by further comprising a step of adding a protecting group of Fmoc to a compound of formula (VI) to obtain a compound of formula (VIII),

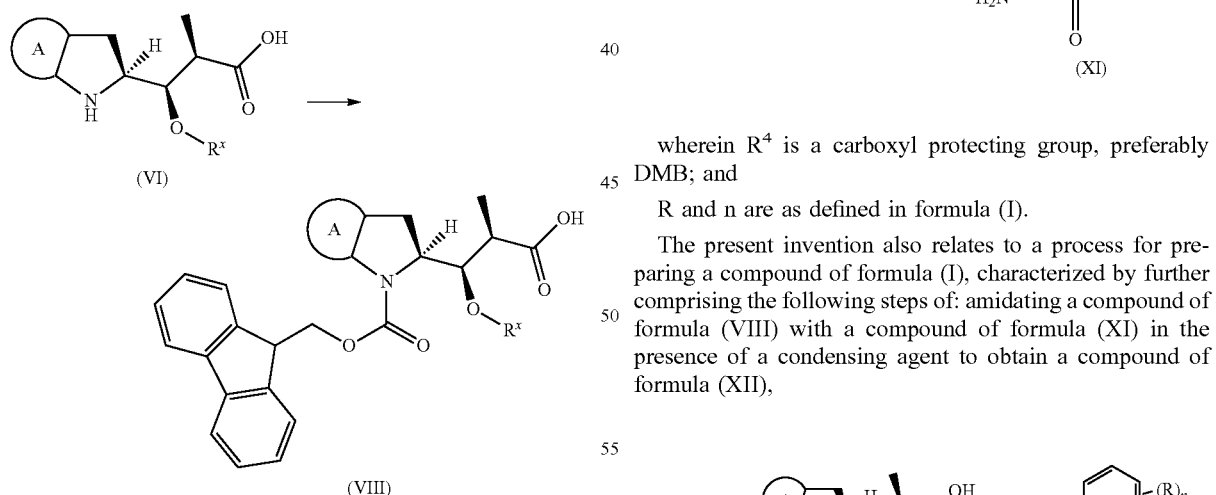

wherein:

A and $R^x$ are as defined in formula (I).

The present invention also relates to a process for preparing a compound of formula (I), characterized by further comprising the following steps of: adding a carboxyl protecting group to a compound of formula (IX) to obtain a compound of formula (X), and removing the Fmoc on the compound of formula (X) to obtain a compound of formula (XI),

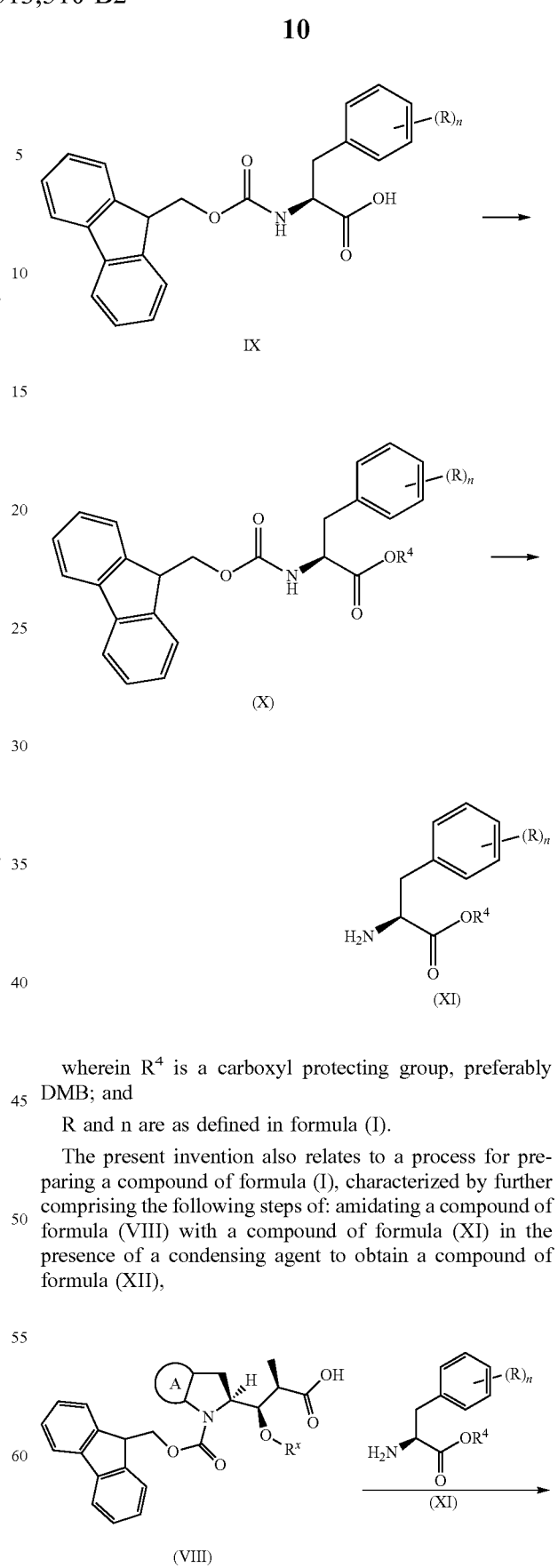

wherein $R^4$ is a carboxyl protecting group, preferably DMB; and

R and n are as defined in formula (I).

The present invention also relates to a process for preparing a compound of formula (I), characterized by further comprising the following steps of: amidating a compound of formula (VIII) with a compound of formula (XI) in the presence of a condensing agent to obtain a compound of formula (XII), -continued

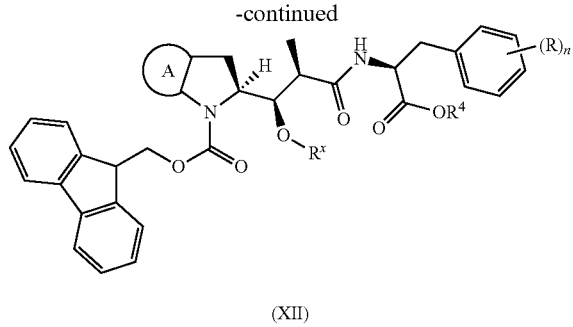

(XII)

wherein the condensing agent is preferably 1-(3-dimethylaminopropyl)-3-1-(3-dimethylaminopropyl)-3-ethylcarbodiimide hydrochloride, N,N'-dicyclohexylcarbodiimide, N,N'-Diisopropylcarbodiimide, O-benzotriazole-N,N,N',N'-tetramethyluronium tetrafluoroborate, 1-1-hydroxybenzotriazole, 1-hydroxy-7-azabenzotriazole, O-benzotriazole-N,N,N',N'—O-benzotriazole-N,N,N',N'-tetramethyluronium hexafluorophosphate, 2-(7-azabenzotriazol)-2-(7-azabenzotriazol)-N,N,N',N'-tetramethyluronium hexafluorophosphate, benzotriazol-1-benzotriazol-1-yloxytris(dimethylamino)-phosphonium hexafluorophosphate or Benzotriazole-1-yl-Benzotriazole-1-yl-oxytripyrrolidino-phosphonium hexafluorophosphate; and more preferably 2-(7-2-(7-azabenzotriazol)-N,N,N',N'-tetramethyluronium hexafluorophosphate; and A, R, R$^4$, R$^x$ and n are as defined in formula (I).

The present invention also relates to a process for preparing a compound of formula (I), characterized by further comprising the following steps of:

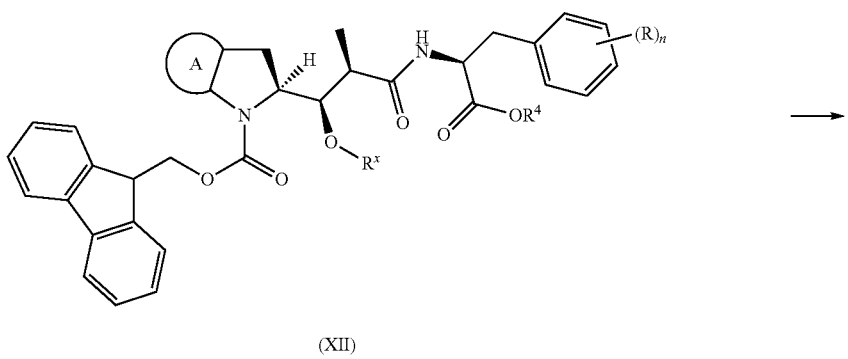

(XII)

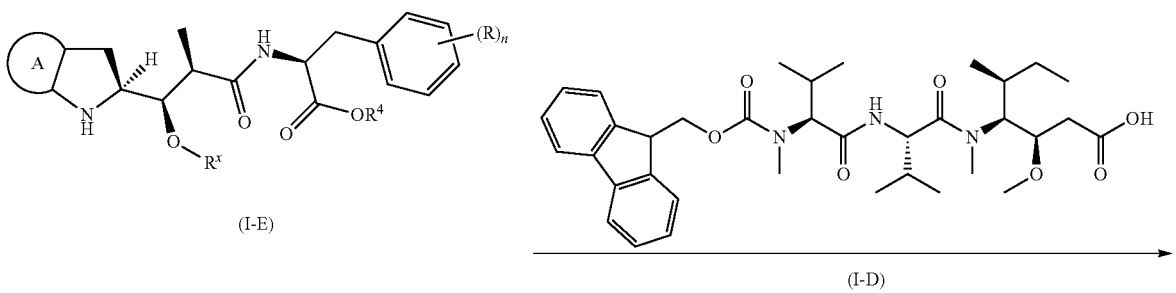

(I-E)                                              (I-D)

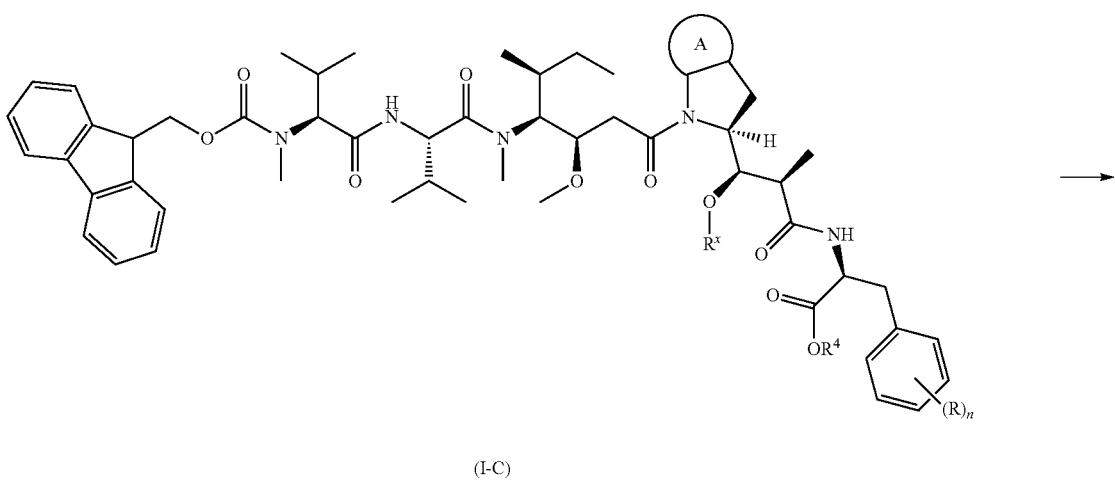

(I-C)

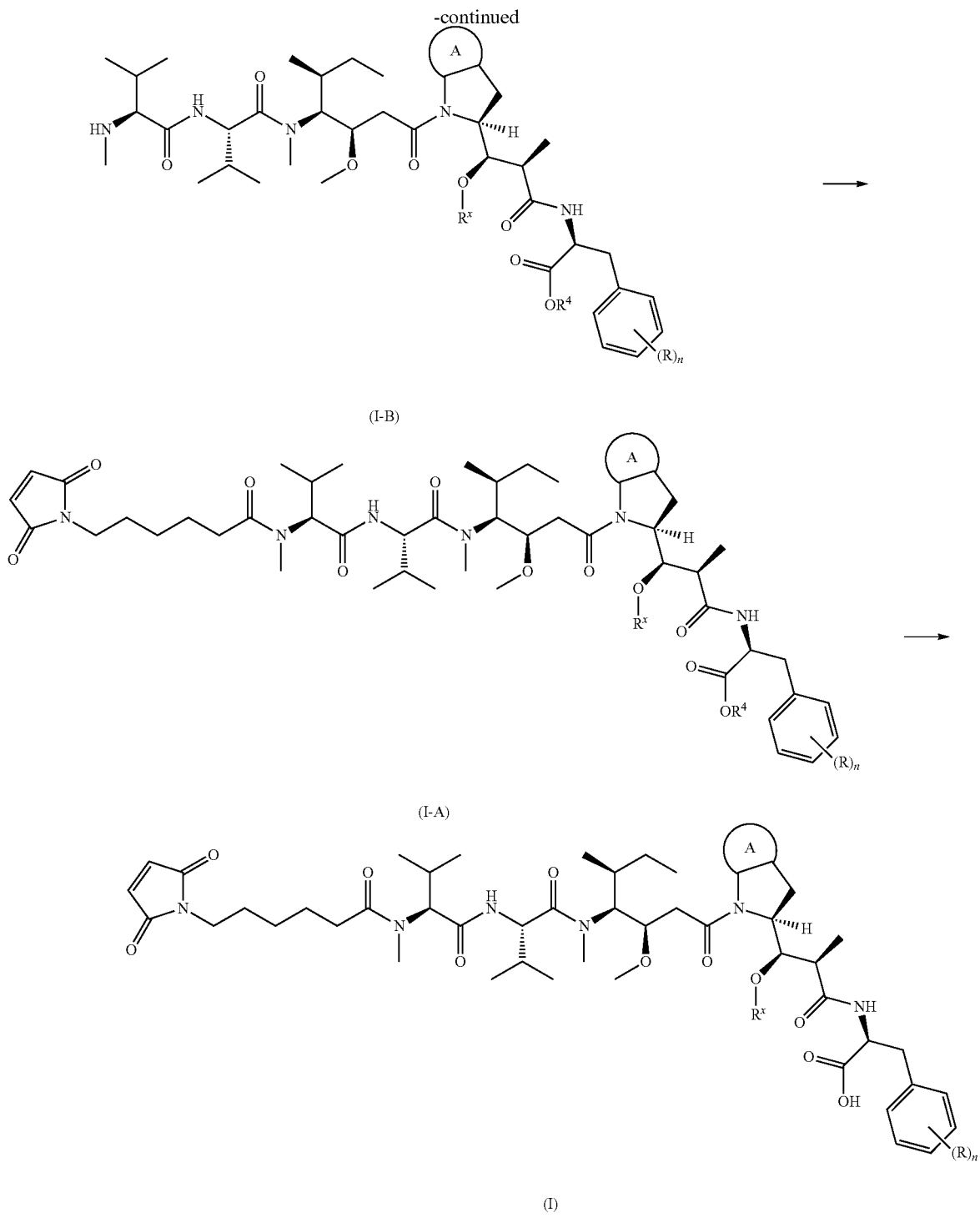

wherein:

removing the protecting group of Fmoc on a compound of formula (XII) under an alkaline condition to obtain a compound of formula (I-E);

amidating the compound of formula (I-E) with a compound of formula (I-D) in the presence of a condensing agent to obtain a chiral intermediate of formula (I-C);

removing the protecting group of Fmoc on the compound of formula (I-C) under an alkaline condition to obtain a chiral compound of formula (I-B);

amidating the compound of formula (I-B) with 6-maleimidocaproic acid in the presence of a condensing agent to obtain a compound of formula (I-A);

removing the carboxyl protecting group on the compound of formula (I-A) under an acidic condition to obtain the target compound of formula (I);

$R^4$ is a carboxyl protecting group, preferably DMB;

A, R, $R^x$ and n are as defined in formula (I).

The present invention also relates to a process for preparing a compound of formula (I), wherein the reagent that provides an alkaline condition in step 1) or step 3) includes an organic base or an inorganic base, wherein the organic base is preferably triethylamine, diethylamine, N,N-diisopropylethylamine, pyridine, sodium bis(trimethylsilyl)amide, n-butyllithium, potassium tert-butoxide or tetrabutylammonium bromide, and the inorganic base is preferably lithium hydroxide, sodium hydroxide, potassium hydroxide, sodium hydride, sodium carbonate, sodium bicarbonate, potassium carbonate, potassium bicarbonate or cesium carbonate; and more preferably diethylamine.

The present invention also relates to a process for preparing a compound of formula (I), wherein the condensing agent in step 2) or step 4) is preferably 1-(3-dimethylaminopropyl)-3-ethylcarbodiimide hydrochloride; N,N'-dicyclohexylcarbodiimide; N,N'-diisopropylcarbodiimide; O-benzotriazole-N,N,N',N'-tetramethyluronium tetrafluoroborate; 1-hydroxybenzotriazole; 1-hydroxy-7-azabenzotriazole; O-benzotriazole-N,N,N',N'-tetramethyluronium hexafluorophosphate; 2-(7-azabenzotriazol)-N,N,N',N'-tetramethyluronium hexafluorophosphate; benzotriazol-1-yloxytris(dimethylamino)-phosphonium hexafluorophosphate or benzotriazole-1-yl-oxytripyrrolidino-phosphonium hexafluorophosphate; and more preferably 2-(7-azabenzotriazol)-N,N,N',N'-tetramethyluronium hexafluorophosphate.

The present invention also relates to a process for preparing a compound of formula (I), wherein the reagent that provides an acidic condition in step 5) is preferably hydrogen chloride solution, hydrochloric acid, nitric acid, phosphoric acid, p-toluenesulfonic acid, $Me_3SiCl$, TMSOTf, trifluoroacetic acid or sulfuric acid, and more preferably trifluoroacetic acid.

The present invention also relates to a process for preparing a compound of formula (I), characterized by further comprising a step of amidating a compound of formula (V) with a compound of formula (XI) in the presence of a condensing agent to obtain a compound of formula (VII),

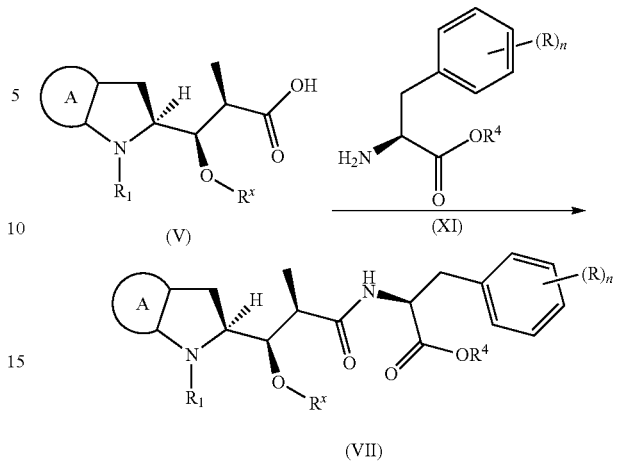

wherein:

the condensing agent is preferably 1-(3-dimethylaminopropyl)-3-ethylcarbodiimide hydrochloride; N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'-tetramethyluronium hexafluorophosphate, 2-(7-azabenzotriazol)-N,N,N',N'-tetramethyluronium hexafluorophosphate, benzotriazol-1-yloxytris(dimethylamino)-phosphonium hexafluorophosphate or benzotriazole-1-yl-oxytripyrrolidino-phosphonium hexafluorophosphate, and more preferably 2-(7-azabenzotriazol)-N,N,N',N'-tetramethyluronium hexafluorophosphate; and $A$, $R^1$, $R$, $R^4$, $R^x$ and n are as defined in formula (I).

The present invention also relates to a process for preparing a compound of formula (I), characterized by further comprising the following steps of:

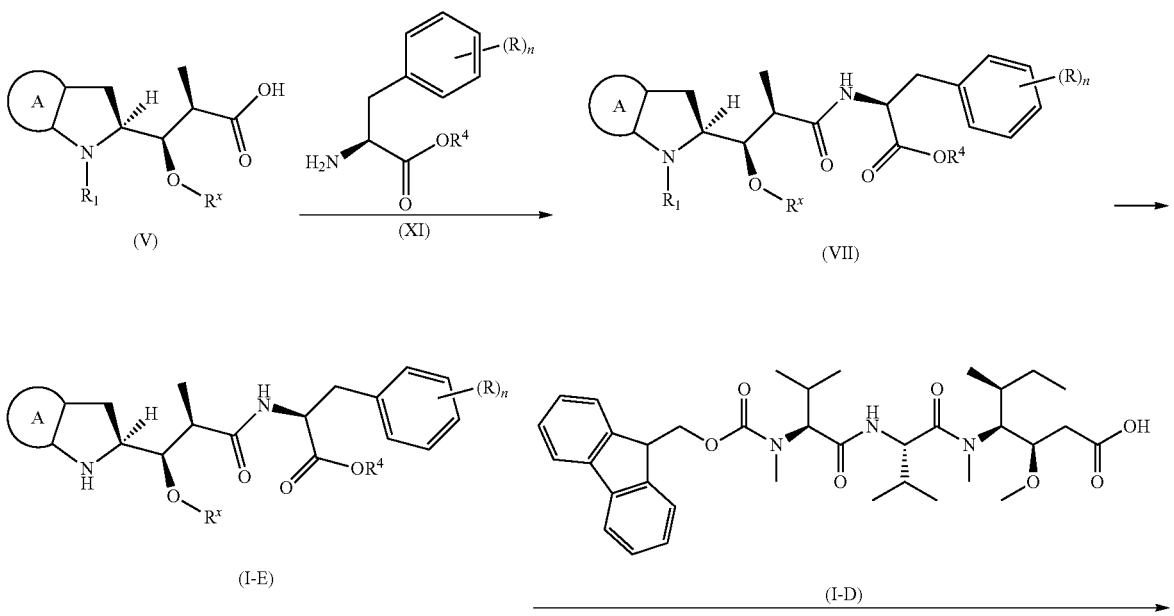

-continued
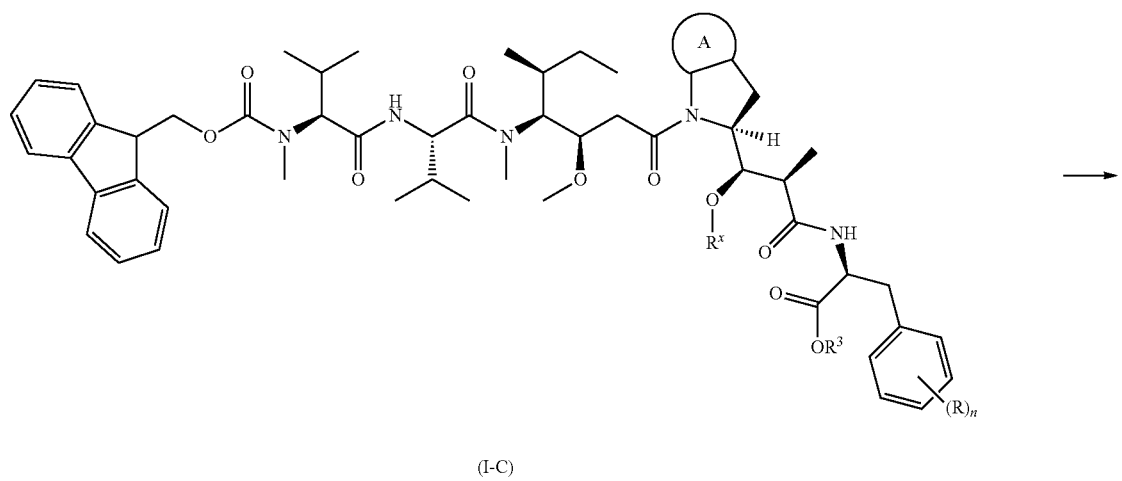
(I-C)
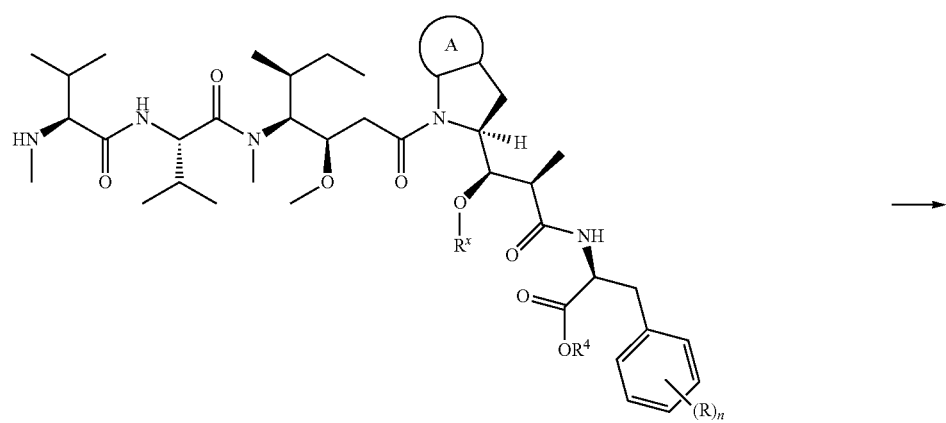
(I-B)
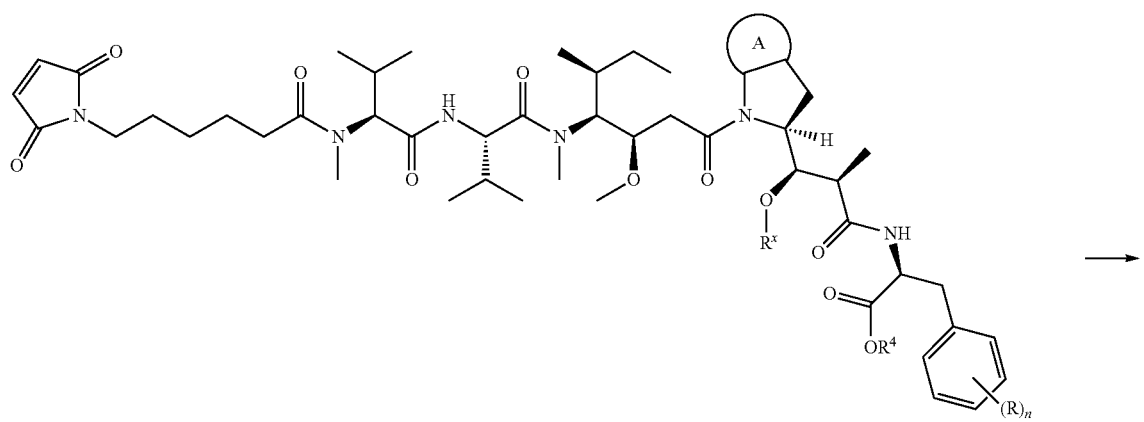
(I-A)

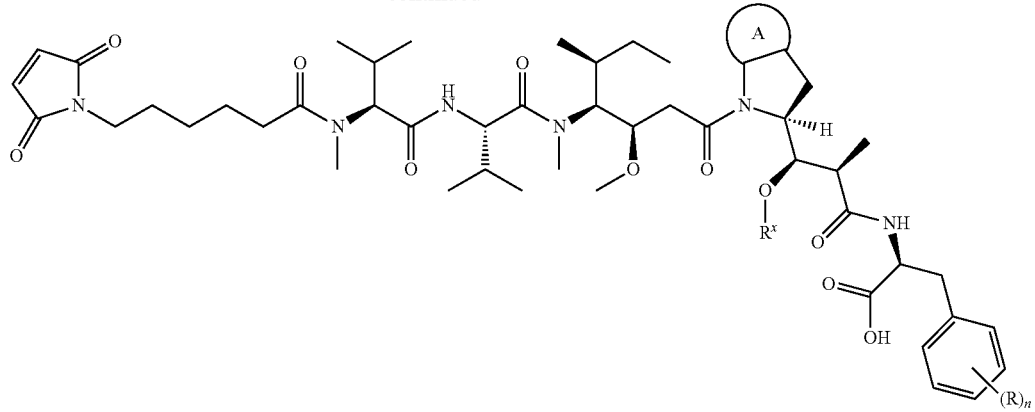

(I)

amidating a compound of formula (V) with a compound of formula (XI) in the presence of a condensing agent to obtain a compound of formula (VII);

removing the amino protecting group on the compound of formula (VII) under an alkaline condition to obtain a compound of formula (I-E);

amidating the compound of formula (I-E) with a compound of formula (I-D) in the presence of a condensing agent to obtain a chiral intermediate of formula (I-C);

removing the protecting group of Fmoc on the compound of formula (I-C) under an alkaline condition to obtain a chiral compound of formula (I-B);

amidating the compound of formula (I-B) with 6-maleimidocaproic acid in the presence of a condensing agent to obtain a compound of formula (I-A);

removing the carboxyl protecting group on compound of formula (I-A) under an acidic condition to obtain the target compound of formula (I);

wherein:

the condensing agent in step 1), step 3) or step 5 is preferably 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'-tetramethyluronium hexafluorophosphate, 2-(7-azabenzotriazol)-N,N,N',N'-tetramethyluronium hexafluorophosphate, benzotriazol-1-yloxytris(dimethylamino)-phosphonium hexafluorophosphate or benzotriazole-1-yl-oxytripyrrolidino-phosphonium hexafluorophosphate, and more preferably 2-(7-azabenzotriazol)-N,N,N',N'-tetramethyluronium hexafluorophosphate;

the reagent that provides an alkaline condition in step 2) or step 4) includes an organic base or an inorganic base, wherein the organic base is preferably triethylamine, diethylamine, N,N-diisopropylethylamine, pyridine, sodium bis(trimethylsilyl)amide, n-butyllithium, potassium tert-butoxide or tetrabutylammonium bromide, and the inorganic base is preferably lithium hydroxide, sodium hydroxide, potassium hydroxide, sodium hydride, sodium carbonate, sodium bicarbonate, potassium carbonate, potassium bicarbonate or cesium carbonate; and more preferably diethylamine, the reagent that provides an acidic condition in step 6) is preferably hydrogen chloride solution, hydrochloric acid, nitric acid, phosphoric acid, p-toluenesulfonic acid, Me₃SiCl, TMSOTf, trifluoroacetic acid or sulfuric acid, and more preferably trifluoroacetic acid;

$R^4$ is a carboxyl protecting group, preferably DMB; and

A, $R^1$, R, $R^x$ and n are as defined in formula (I).

A compound of formula (VIII) in the present invention can be synthesized by one-pot method, comprising the steps of removing the carboxyl and amino protecting groups on a compound of formula (IV) and then adding a protecting group of Fmoc to obtain the compound of formula (VIII),

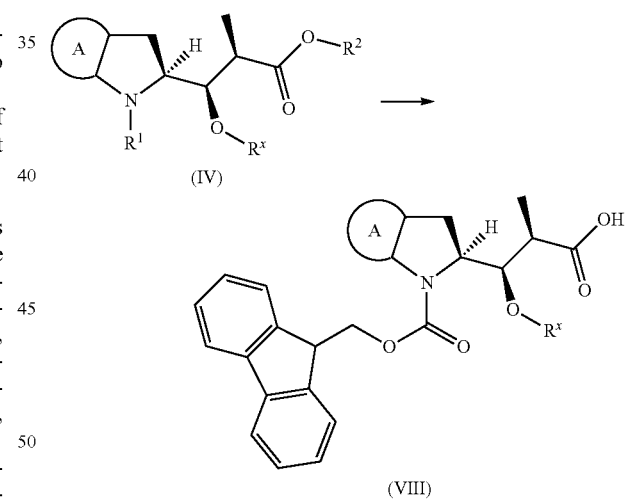

wherein:

A, $R^1$, $R^2$ and $R^x$ are as defined in formula (I).

The preparation process of a novel toxin of formula (I) according to the present invention has the characteristics of simple operation, mild reaction conditions, high optical purity, high synthesis efficiency, high synthesis yield, suitability for industrial production, and significant social and economic benefits.

In a preferred embodiment of the present invention, in the compounds of each formula, ring A has the same structure, selected from a 3 to 8 membered ring, preferably a 3 membered ring; in particular, the ring is a cycloalkyl ring.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-2-methylhexyl, 3-methylhexyl, 4-methylhexyl, 5-methylhexyl, 2,3-dimethylpentyl, 2,4-2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomer chain thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-1,2-dimethylpropyl, 2,2-dimethylpropyl, 1-ethylpropyl, 2-methylbutyl, 3-methylbutyl, n-hexyl, 1-1-ethyl-2-methylpropyl, 1,1,2-trimethylpropyl, 1,1-dimethylbutyl, 1,2-dimethylbutyl, 2,2-2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When the substituent group(s) can be substituted at any available connection point, preferably the group(s) is one or more groups independently selected from the group consisting of alkyl, alkenyl, alkynyl, alkyxoy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylic alkylthio, oxo group, carboxyl and alkoxycarbonyl.

"Cycloalkyl" refers to a saturated and/or partially unsaturated monocyclic or polycyclic hydrocarbon group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called as spiro atom), wherein one or more rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

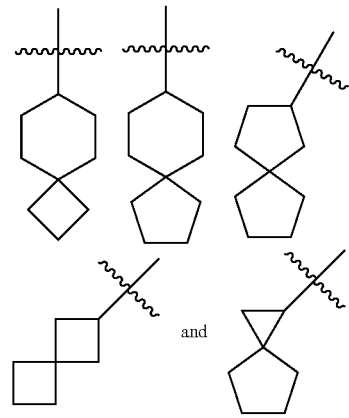

"Fused cycloalkyl" refers to a 5 to 20 membered full-carbon polycyclic group, wherein each ring in the system shares an adjacent pair of carbon atoms with another ring, wherein one or rings can contain one or more double bonds, but none of the rings has a completely conjugated pi-pi-electron system, preferably 6 to 14 membered fused cycloalkyl, more preferably 7 to 10 fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyl include:

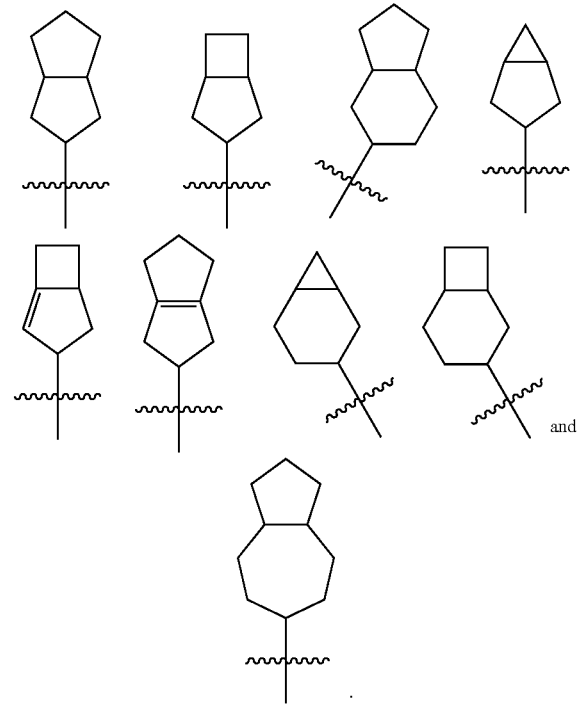

"Bridged cycloalkyl" refers to a 5 to 20 membered full-carbon polycyclic group, wherein every two rings in the system share two disconnected carbon atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyl include:

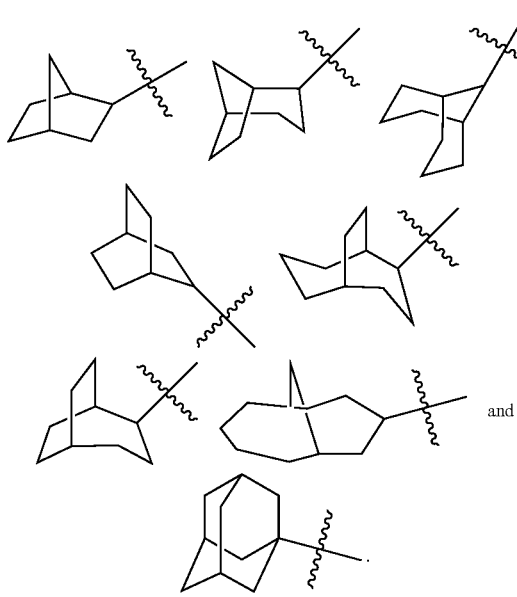

The aforementioned cycloalkyl can be fused to the ring of aryl, heteroaryl or wherein the ring bound to the parent structure is cycloalkyl. Non-limiting examples include indanyl, tetrahydronaphthyl, benzocydoheptyl and the like. The cycloalkyl can be optionally substituted or unsubstituted. When substituted, the substituent group(s) is preferably one or more groups independently selected from the group consisting of alkyl, alkenyl, alkynyl, alkyxoy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo group, carboxyl and alkoxycarbonyl.

"Heterocyclyl" refers to a 3 to 20 membered saturated and/or partially unsaturated monocyclic or polycyclic hydrocarbon group having one or more heteroatoms selected from the group consisting of N, O, and $S(O)_m$ (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms, wherein 1 to 4 atoms are heteroatoms, more preferably 3 to 8 atoms wherein 1 to 3 atoms are heteroatoms, and most preferably 5 to 6 atoms wherein 1 to 2 or 1 to 3 atoms are heteroatoms. Non-limiting examples of monocyclic heterocyclyl include, pyrrolidyl, imidazolidinyl, tetrahydrofuranyl, tetrahydrothiophenyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl, azetidinyl and the like, preferably 1,2,5-oxadiazolyl, pyranyl, piperidinyl, azetidinyl, pyrrolidinyl or morpholinyl. Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called as a spiro atom), wherein said rings have one or more heteroatoms selected from the group consisting of N, O, and $S(O)_m$ (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

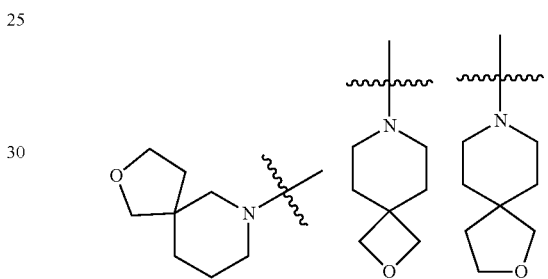

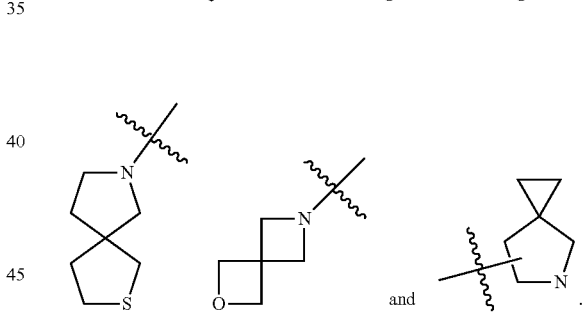

"Fused heterocyclyl" refers to a 5 to 20 membered polycyclic heterocyclyl group, wherein each ring in the system shares an adjacent pair of carbon atoms with another ring, wherein one or more rings can contain one or more double bonds, but none of the rings has a completely conjugated pi-electron system, and wherein the rings have one or more heteroatoms selected from the group consisting of N, O, and $S(O)_p$ (wherein p is an integer of 0 to 2) as ring atoms, with the remaining ring atoms being carbon atoms, preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyl include:

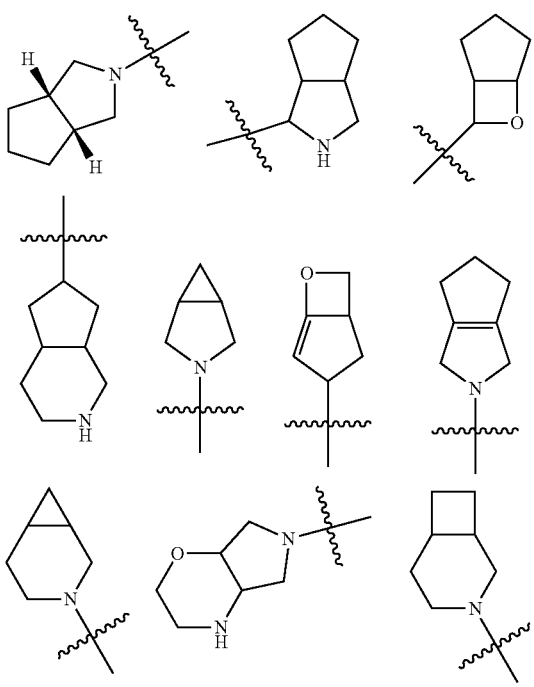

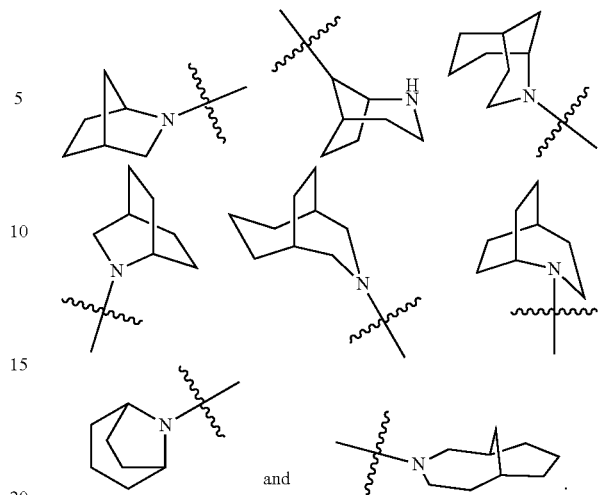

The heterocyclyl ring can be fused to the ring of aryl, heteroaryl or cycloalkyl, wherein the ring bound to the parent structure is heterocyclyl. Non-limiting examples include:

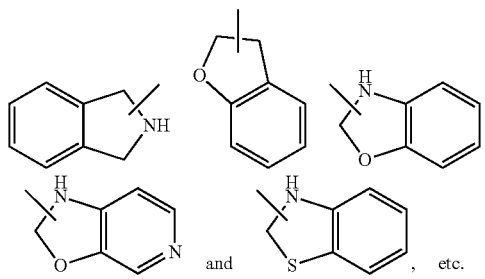

The heterocyclyl can be optionally substituted or unsubstituted. When substituted, the substituent group(s) is preferably one or more group(s) independently selected from the group consisting of alkyl, alkenyl, alkynyl, alkyxoy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylic alkylthio, oxo group, carboxyl and alkoxycarbonyl.

"Aryl" refers to a 6 to 14 membered full-carbon monocyclic ring or polycyclic fused ring (i.e., each ring in the system shares an adjacent pair of carbon atoms with another ring in the system) having a conjugated pi-electron system, preferably 6 to 10 membered aryl, for example, phenyl and naphthyl, and most preferably phenyl. The aryl ring can be fused to the ring of heteroaryl, heterocyclyl or cycloalkyl, wherein the ring bound to the parent structure is aryl ring. Non-limiting examples include:

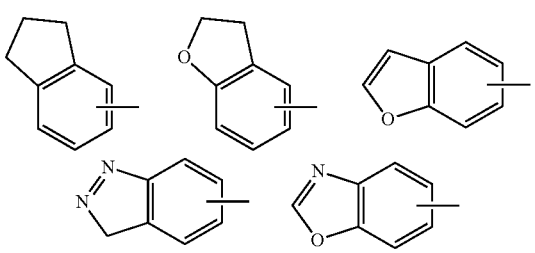

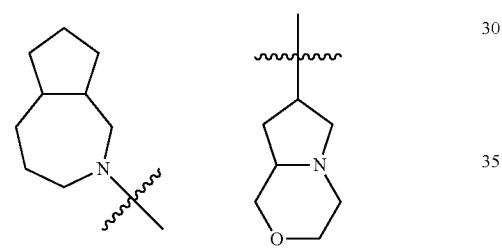

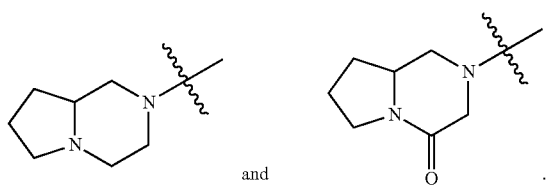

and

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S(O)$_m$ (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyl include:

-continued

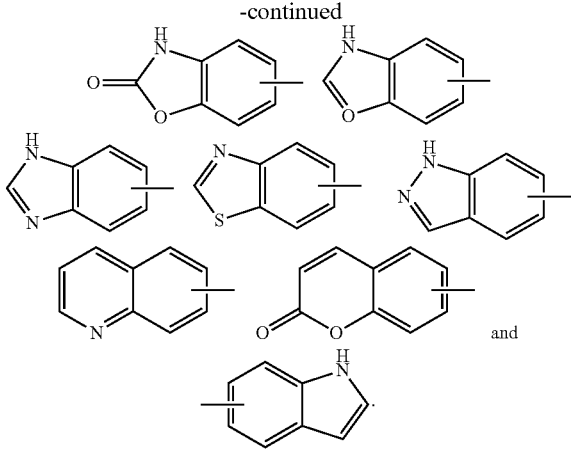

The aryl group can be optionally substituted or unsubstituted. When substituted, the substituent group(s) is preferably one or more groups independently selected from the group consisting of alkyl, alkenyl, alkynyl, alkyxoy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylic alkylthio, carboxyl and alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl having 1 to 3 heteroatoms, more preferably 5 or 6 membered heteroaryl having 1 to 2 said heteroatoms, for example, imidazolyl, furyl, thienyl, thiazolyl, pyrazolyl, oxazolyl, pyrrolyl, tetrazolyl, pyridinyl, pyrimidinyl, thiadiazole, pyrazinyl and the like, preferably imidazolyl, thiazolyl, pyrazolyl or pyrimidinyl, thiazolyl, and more preferably pyrazolyl or thiazolyl. The heteroaryl can be fused with the ring of aryl, heterocyclyl or cycloalkyl, wherein the ring bound to the parent structure is heteroaryl ring. Non-limiting examples include:

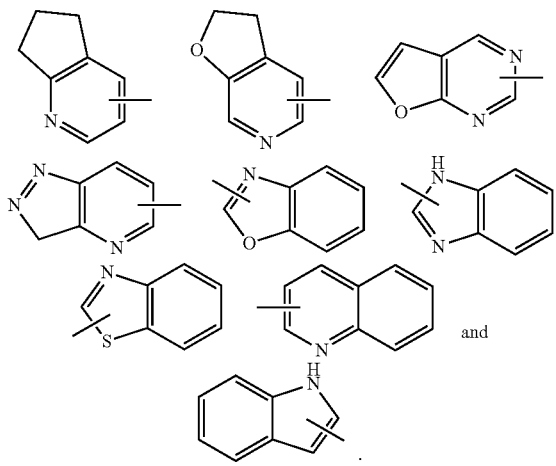

The heteroaryl can be optionally substituted or unsubstituted. When substituted, the substituent group(s) is preferably one or more groups independently selected from the group consisting of alkyl, alkenyl, alkynyl, alkyxoy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocylic alkylthio, carboxyl and alkoxycarbonyl.

"Hydroxy" refers to an —OH group.
"Halogen" refers to fluorine, chlorine, bromine or iodine.
"Amino" refers to a —$NH_2$ group.
"Oxo group" refers to a =O group.

The 3 to 8 membered ring is selected from the group consisting of carbocyclic and heterocyclic ring, wherein the heterocyclic ring comprises several heteroatoms such as N, O and S.

"Optional" or "optionally" means that the event or circumstance described subsequently can, but need not, occur, and such a description includes the situation in which the event or circumstance does or does not occur. For example, "the heterocyclyl group optionally substituted by an alkyl" means that an alkyl group can be, but need not be, present, and such a description includes the situation of the heterocyclyl group being substituted by an alkyl and the heterocyclyl group not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy group having free hydrogen and carbon atoms having unsaturated bonds (such as olefinic) can be unstable.

In the present invention, different terms, such as "X is selected from the group consisting of A, B or C," "X is selected from the group consisting of A, B and C," "X is A, B or C" and "X is A, B and C," are the same meaning. It means that X can be any one or more of A, B, and C.

Abbreviation Table

| Abbreviation | Full name |
| --- | --- |
| Me | Methyl |
| Boc | Tert-butyloxycarbonyl |
| t-Bu | Tert-butyl |
| Bn | Benzyl |
| Ph | Phenyl |
| Tosyl | p-Toluenesulfonyl |
| Fmoc | 9-Fluorenylmethoxycarbonyl |
| Alloc | Allyloxycarbonyl |
| Troc | Trichloroethoxycarbonyl |
| Teoc | Trimethylsilyl ethoxycarbonyl |
| Nosyl | p-Nitrophenylsulfonyl |
| TMSOTf | Trimethylsilyl trifluoromethanesulfonate |
| Cbz | Benzyloxycarbonyl |
| PfP | Pentafluorophenyl |
| PMB | p-Methylbenzyl |
| MEM | Methoxyethoxymethyl |
| Allyl | Allyl |
| DMB | 2,4-Dimethoxybenzyl |

PREFERRED EMBODIMENTS

The present invention will be further described with reference to the following examples so that the person skilled in the art can understand the present invention more completely. The specific examples are only used to illustrate the technical solutions of the present invention, and do not limit the present invention in any way.

EXAMPLES

The structures of the compounds are identified by nuclear magnetic resonance (NMR) and/or mass spectrometry (MS). NMR chemical shifts (δ) are given in $10^{-6}$ (ppm). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS).

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

Chiral HPLC analysis is determined on a LC-10A vp (Shimadzu) or SFC-analytical (Berger Instruments Inc.).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

Prep Star SD-1 (Varian Instruments Inc.) or SFC-multi-gram (Berger Instruments Inc.) is used for chiral preparative column chromatography.

The average kinase inhibition rates and IC$_{50}$ values are determined by a NovoStar ELISA (BMG Co., Germany).

The known starting materials of the present invention can be prepared by the conventional synthesis methods in the art, or can be purchased from ABCR GmbH & Co. KG, Acros Organics, Aldrich Chemical Company, Accela ChemBio Inc., or Dari Chemical Company, Unless otherwise stated, the reactions are carried out under nitrogen atmosphere or argon atmosphere.

The term "nitrogen atmosphere" or "argon atmosphere" means that a reaction flask is equipped with a 1 L nitrogen or argon balloon.

The term "hydrogen atmosphere" means that a reaction flask is equipped with a 1 L hydrogen balloon.

Pressurized hydrogenation reactions are performed with a Parr 3916EKX hydrogenation instrument and a QL-500 hydrogen generator or HC2-SS hydrogenation instrument.

In hydrogenation reactions, the reaction system is generally vacuumed and filled with hydrogen, with the above operations repeated three times.

CEM Discover-S 908860 type microwave reactor is used in microwave reaction.

Unless otherwise stated, the solution used in the reactions refers to an aqueous solution.

Unless otherwise stated, the reaction temperature in the reactions refers to room temperature, ranging from 20° C. to 30° C.

The reaction process is monitored by thin layer chromatography (TLC), and the developing solvent system includes: A: dichloromethane and methanol system, B: n-hexane and acetate system, C: petroleum ether and ethyl acetate system, D: acetone. The ratio of the volume of solvent can be adjusted according to the polarity of the compounds.

The elution system for purification of the compounds by column chromatography, thin layer chromatography and CombiFlash flash rapid preparation instrument includes: A: dichloromethane and methanol system, B: n-hexane and ethyl acetate system, C: dichloromethane and acetone system. The ratio of the volume of the solvent can be adjusted according to the polarity of the compounds, and sometimes a little alkaline reagent, such as triethylamine, or acidic reagent, such as acetic acid, can be added.

Synthesis Example 1 Method 1

(S)-2-((2R,3R)-3-((1S,3S,5S)-2-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)-2-azabicyclo[3.1.0]hexan-3-yl)-3-methoxy-2-methylpropanamido)-3-(2-fluorophenyl) propanoic Acid

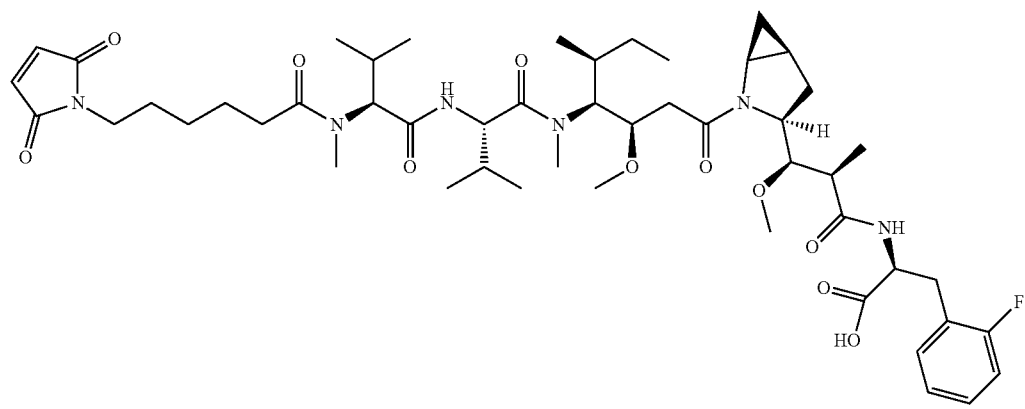

-continued
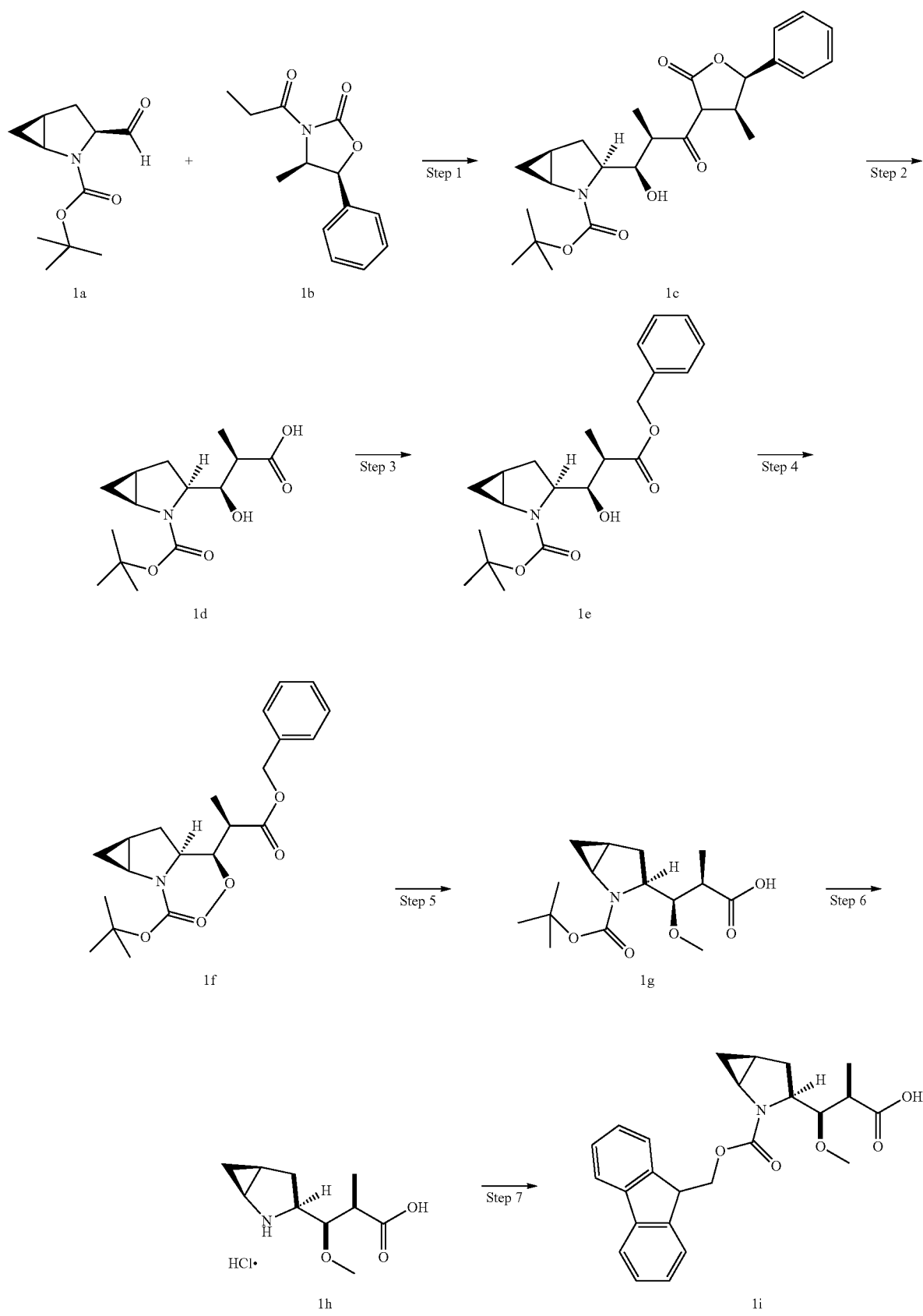

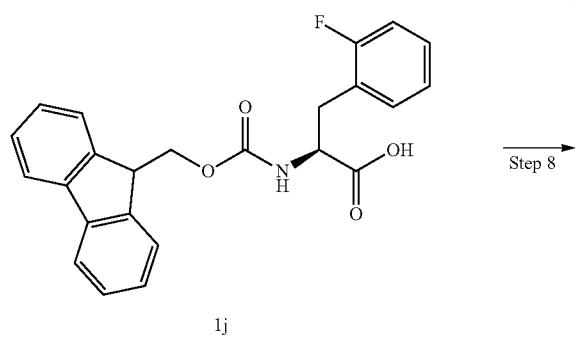
1j
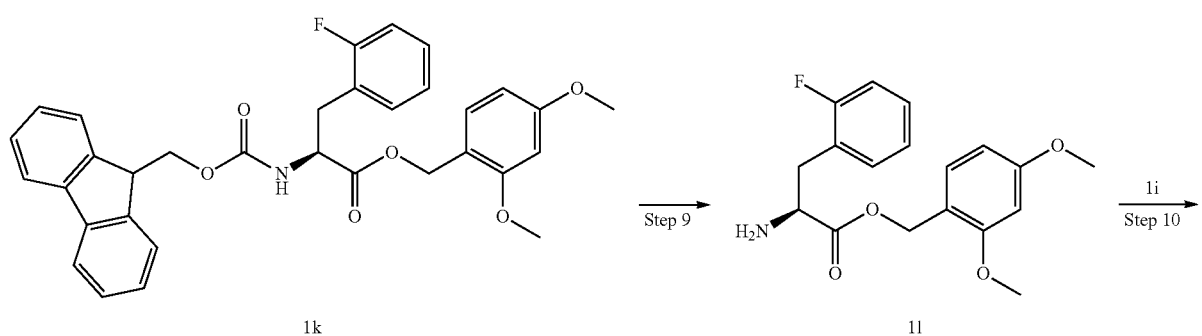
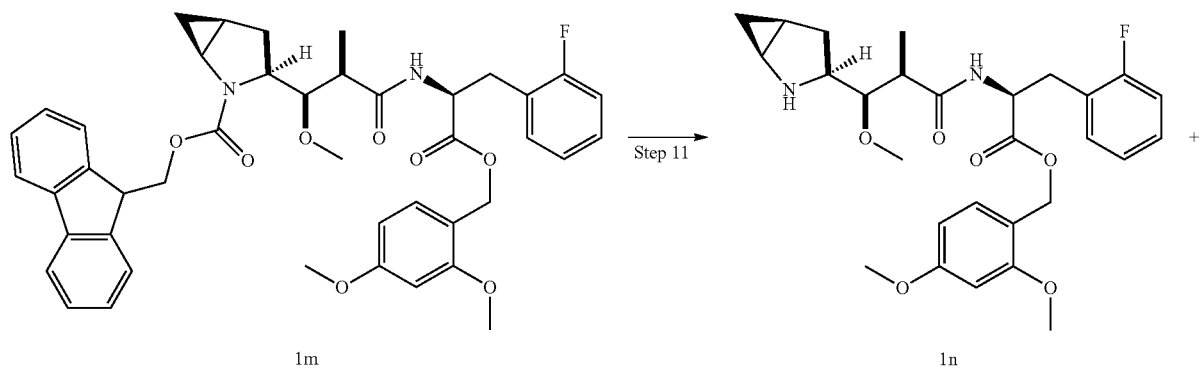
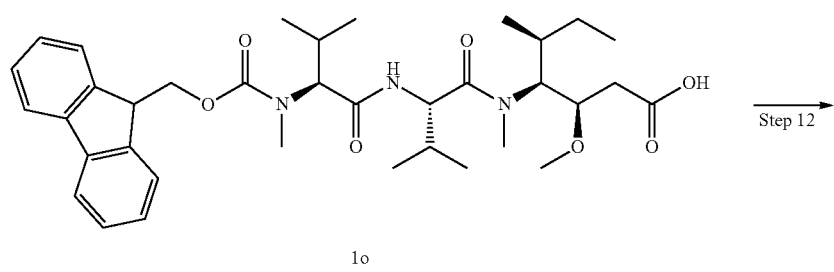

-continued
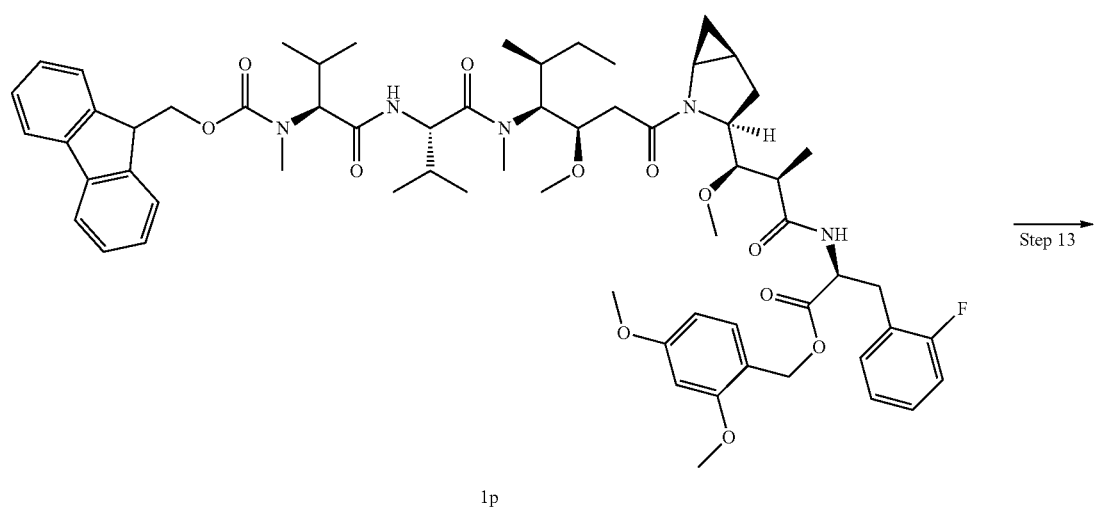
1p
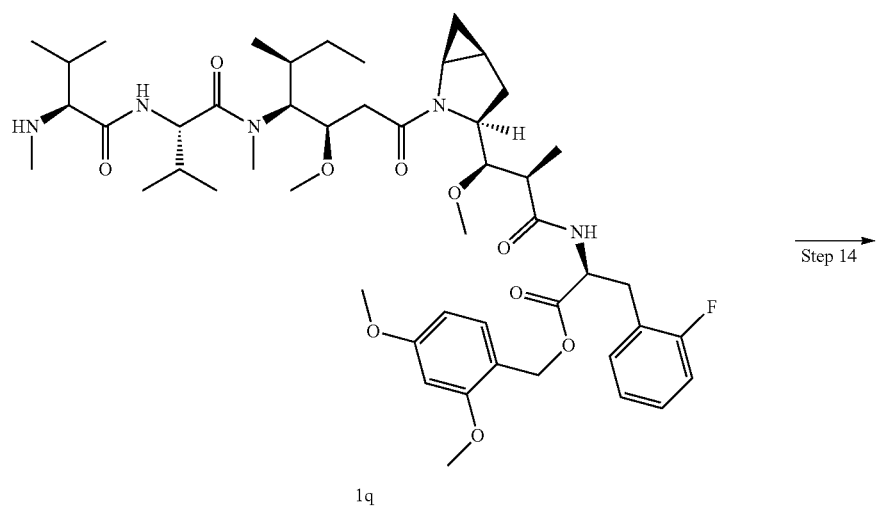
1q
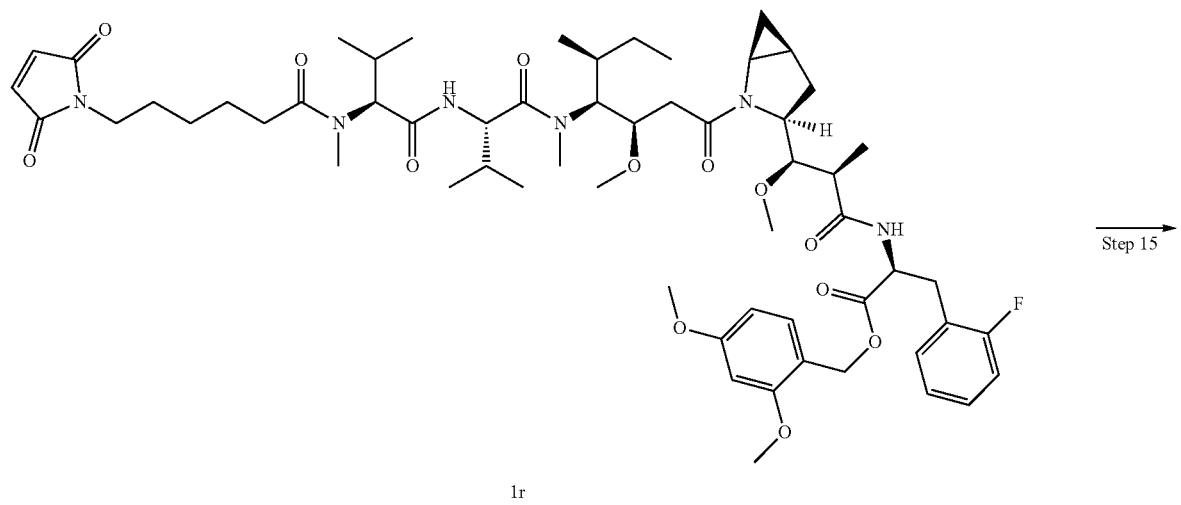
1r

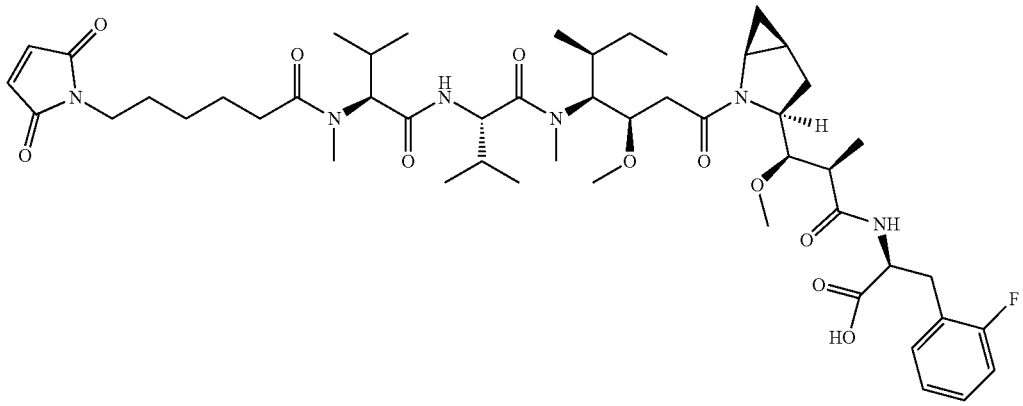 [SMILES: CC[C@H](C)[C@@H]([C@@H](CC(=O)N1[C@H]2C[C@H]2C[C@H]1[C@H](OC)[C@@H](C)C(=O)N[C@@H](Cc1ccccc1F)C(=O)O)OC)N(C)C(=O)[C@@H](NC(=O)[C@H](C(C)C)N(C)C(=O)CCCCCN1C(=O)C=CC1=O)C(C)C]

Step 1

(1S,3S,5S)-tert-butyl 3-((1R,2R)-1-hydroxy-2-methyl-3-((4R,5S)-4-methyl-2-oxo-5-phenyloxazolidin-3-yl)-3-oxopropyl)-2-azabicyclo[3.1.0]hexane-2-carboxylate (4R,5S)-4-methyl-5-phenyl-3-propionyloxazolidin-2-one 1b (14.7 g, 63.1 mmol) was dissolved in 120 mL dichloromethane, and cooled to 0° C. in an ice bath. Triethylamine (9.7 mL, 72.6 mmol) and dibutylboron trifluoromethanesulfonate (65 mL, 65 mmol) was added. After completion of the addition, the reaction solution was stirred for 1 hour. The reaction solution was cooled to −78° C. in a dry ice-acetone bath. (1S,3S,5S)-tert-butyl 3-formyl-2-azabicyclo[3.1.0]hexane-2-3-formyl-2-azabicyclo[3.1.0]hexane-2-carboxylate 1a (12 g, 56.8 mmol, prepared by a method disclosed in the patent application "WO2008081399") was dissolved in 10 mL of dichloromethane, and the above solution was added into the reaction solution. After completion of the addition, the reaction solution was stirred for 2 hours. The dry ice-acetone bath was removed, and the reaction solution was naturally warmed up to 0° C. and reacted for 1.5 hours at 0° C. Then, 100 mL of a mixed solution of phosphate buffer (pH=7.0) and methanol (V:V=1:3) were added into the reaction solution, followed by addition of 100 mL of a mixed solution of methanol and hydrogen peroxide (30%) (V:V=2:1). The resulting reaction solution was stirred for 30 minutes, and then the organic phase was evaporated under reduced pressure. The remaining aqueous phase was extracted with dichloromethane (150 mL×3). The organic phases were combined, washed with water (100 mL×2) and saturated sodium chloride solution (100 mL×2), dried over anhydrous sodium sulfate, and filtered. The filtrate was concentrated under reduced pressure, and the resulting residue was purified by silica gel column chromatography with elution system C to obtain the title product 1c (15.6 g, white powder) in a yield of 72.3%.

MS m/z (ESI): 445.4 [M+1]

Step 2

(2R,3R)-3-((1S,3S,5S)-2-(tert-butoxycarbonyl)-2-azabicyclo[3.1.0]hexan-3-yl)-3-hydroxy-2-methylpropanoic Acid Compound 1c (15.7 g, 35.3 mmol) was added into 500 mL tetrahydrofuran. Hydrogen peroxide (15.3 g, 134 mmol) was slowly added to the resulting solution in an ice bath and the temperature of the reaction solution was controlled at 0° C., followed by addition of lithium (2.5 g, 60 mmol). After completion of the addition, the ice bath was removed and the reaction was naturally warmed up to room temperature. The reaction solution was stirred for 16 hours. sulfite (17.8 g, 141.2 mmol) was slowly added to the above reaction in batches in an ice bath. After completion of the addition, the reaction solution was stirred for 30 minutes and 150 mL of water added. The ice bath was removed and the organic phase was evaporated under reduced pressure. The remaining aqueous phase was washed with dichloromethane (150 mL×3). 2N of hydrochloric acid was added dropwise in an ice bath to adjust the pH to 2-3. The mixture was extracted with ethyl acetate (100 mL×3), washed with water (500 mL) and saturated sodium chloride solution (500 mL), dried over anhydrous sodium sulfate, and filtered. The filtrate was concentrated under reduced pressure to obtain the title product 1d (9.3 g, white solid) in a yield of 92%.

MS m/z (ESI): 284.3 [M−1]

Step 3

(1S,3S,5S)-tert-butyl 3-((1R,2R)-3-(benzyloxy)-1-hydroxy-2-methyl-3-oxopropyl)-2-azabicyclo[3.1.0]hexane-2-carboxylate Compound 1d (9.3 g, 32.6 mmol) was dissolved in 120 mL of N,N-dimethylformamide. After cooling to 0° C. in an ice bath, sodium bicarbonate (15.06 g, 179.3 mmol) and benzyl bromide (27.9 g, 163.1 mmol) were added. After completion of the addition, the ice bath was removed, and the reaction solution was stirred at 20° C. for 16 hours. Then, 200 mL of saturated ammonium chloride solution were added to quench the reaction in an ice bath. The reaction solution was extracted with ethyl acetate (150 mL×3). The organic phase was washed with water (200 mL) and saturated sodium chloride solution (150 mL) successively, dried over anhydrous sodium sulfate, and filtered. The filtrate was concentrated under reduced pressure, and the resulting residue was purified by silica gel column chromatography with elution system C to obtain the title product 1e (10.3 g, oil) in a yield of 84.2%.

MS m/z (ESI): 376.4 [M+1]

Step 4

(1S,3S,5S)-tert-butyl 3-((1R,2R)-3-(benzyloxy)-1-methoxy-2-methyl-3-oxopropyl)-2-azabicyclo[3.1.0]hexane-2-carboxylate Compound 1e (10.3 g, 27.4 mmol) was dissolved in 90 mL of N-methyl pyrrolidone. Methyl iodide (18 mL, 234 mmol) was added, and 60% sodium hydride (1.28 g, 32.1 mmol) was added in batches, and the reaction solution was stirred for 30 minutes. Then, 200 mL of saturated ammonium chloride solution were cooled to 0° C. in an ice bath, and then added into the reaction solution and stirred for 10 minutes. The reaction solution was extracted with ethyl acetate (300 The organic phase was washed with water (200 mL×2) and saturated sodium chloride solution (200 mL) successively, dried over anhydrous sodium sulfate, and filtered. The filtrate was concentrated, and the resulting residue was purified by silica gel column chromatography with elution system C to obtain the title product 1f (9.3 g, oil) in a yield of 87.2%.

MS M/Z (ESI): 390.4 [M+1]

Step 5

(2R,3R)-3-((1S,3S,5S)-2-(tert-butoxycarbonyl)-2-azabicyclo[3.1.0]hexan-3-yl)-3-methoxy-2-methyl-propanoic Acid Compound 1f (9.3 g, 23.88 mmol) was dissolved in 90 mL of tetrahydrofuran, and palladium-carbon (10%, 1.86 g) was added. The reaction system was purged three times with hydrogen. The reaction solution was heated to 35° C. and stirred for 30 minutes. The reaction solution was filtered through celite. The filtrate was concentrated and dried to obtain the crude title product 1g (8.2 g, oil) in a crude yield of about 100%. The product was used directly in the next step without further purification.

Step 6

(2R,3R)-3-((1S,3S,5S)-2-azabicyclo[3.1.0]hexan-3-yl)-3-methoxy-2-methylpropanoic Acid Hydrochloride The crude product 1g (8.3 g, 27.7 mmol) was dissolved in a solution of hydrochloric acid in 1,4-dioxane (5.0M, 50 mL), and stirred for 30 minutes. The reaction solution was concentrated under reduced pressure and dried to obtain the crude title product 1h (8.2 g, light yellow liquid) in a crude yield of about 100%. The product was used directly in the next step without further purification.

Step 7

(2R,3R)-3-((1S,3S,5S)-2-(((9H-fluoren-9-yl)methoxy)carbonyl)-2-azabicyclo[3.1.0]hexan-3-yl)-3-methoxy-2-methylpropanoic Acid The crude product 1h (8.2 g, 41.2 mmol) was dissolved in 70 mL of water, and 70 mL of 1,4-dioxane was added. After cooling to 0° C. in an ice bath, N, N-diisopropylethylamine (31.9 g, mmol) was added to the above reaction solution. N-(9-Fluorenylmethoxycarbonyloxy)succinimide (18.06 g, 53.56 mmol) was dissolved in 70 mL of 1,4-dioxane. The above solution was added into reaction solution. After completion of the addition, the ice bath was removed, and the reaction solution was naturally warmed up to room temperature. The reaction solution was then stirred for hours. The organic phase was evaporated under reduced pressure, and then 100 mL of water were added to the reaction solution. 1N of hydrochloride acid was added dropwise until the pH of the reaction solution was 2. The mixture was extracted with dichloromethane (300 mL×3). The organic phase was washed with water (300 mL×2) and saturated sodium chloride solution (300 mL) successively, dried over anhydrous sodium sulfate, and filtered. The filtrate was concentrated under reduced pressure, and the resulting residue was purified by silica gel column chromatography with elution system A to obtain the title product 1i (8.7 g, white foamy solid) in a yield of 85%.

MS m/z (ESI): 422.4 [M+1]

Step 8

(S)-2,4-dimethoxybenzyl 2-((((9H-fluoren-9-yl)methoxy)carbonyl)amino)-3-(2-fluorophenyl)propanoate (S)-2-((((9H-fluoren-9-yl)methoxy)carbonyl)amino)-3-(2-fluorophenyl)propanoic acid 1j (13 g, 32.6 mmol) was dissolved in 50 mL of dichloromethane, and 3,5-dimethanoxybenzyl alcohol (5.93 g, 35.27 mmol) was added, followed by dropwise addition of N,N-dimethylformamide dimethyl acetal (8.9 mL, 36.8 mmol). After completion of the addition, the reaction solution was stirred for 40 hours. The reaction solution was washed with water (50 mL) and saturated sodium chloride solution (50 mL) successively, dried over anhydrous sodium sulfate, and filtered. The filtrate was concentrated under reduced pressure, and the resulting residue was purified by silica gel column chromatography with elution system C to obtain the title product 1k (34.2 g, white solid) in a crude yield of about 100%. The product was used directly in the next step without further purification. MS m/z (ESI): 556.4 [M+1]

Step 9

(S)-2,4-dimethoxybenzyl 2-amino-3-(2-fluorophenyl)propanoate

Compound 1k (17 g, 30.6 mmol) was dissolved in 40 mL of dichloromethane, then diethylamine (80 mL, 0.78 mmol) was added and stirred for 3 hours. The reaction solution was concentrated under reduced pressure, and the resulting residue was purified by silica gel column chromatography with elution system A to obtain the title product 1l (7.8 g, white viscous material) in a yield of 76.4%.

MS m/z (ESI): 334.3 [M+1]

Step 10

(1S,3S,5S)-(9H-fluoren-9-yl)methyl 3-((1R,2R)-3-(((S)-1-((2,4-dimethoxybenzyl)oxy)-3-(2-fluorophenyl)-1-oxopropan-2-yl)amino)-1-methoxy-2-methyl-3-oxopropyl)-2-azabicyclo[3.1.0]hexane-2-carboxylate Condition 1:

Compound 1i (2.5 g, 5.94 mmol) and compound 1l (2.04 g, 5.94 mmol) were dissolved in 36 mL of a mixed solution of dichloromethane and N,N-dimethylformamide (V:V=5:1), followed by addition of 2-(7-azabenzotriazol)-N,N,N',N'-tetramethyluronium hexafluorophosphate (2.7 g, 7.13 mmol) and N,N-diisopropylethylamine (3.1 mL, 17.8 mmol). After completion of the addition, the reaction solution was stirred for 1 hour at 20° C. Then, 100 mL of water were added into the reaction solution. The mixture was then stirred, and two phases were separated. The organic phase was washed with water (100 mL×2) and saturated sodium chloride solution (100 mL) successively, dried over anhydrous sodium sulfate, and filtered. The filtrate was concentrated under reduced pressure, and the resulting residue was purified by silica gel column chromatography with elution system C to obtain the title product 1m (3.9 g, white foamy solid) in a yield of 89.2%.

Condition 2:

Compound 1i (9.1 g, 21.62 mmol), compound 1l (7.5 g, 22.69 mmol) and HATU [2-(7-azabenzotriazole)-N,N,N',N'-tetramethyluronium hexafluorophosphate] (9.9 g, 25.94 mmol) were dissolved in 120 mL of a mixed solution of dichloromethane and N,N-dimethylformamide (V:V=5:1), followed by addition of N,N-diisopropylethylamine (8.4 g, 64.89 mmol). The reaction solution was stirred for 1 hour at 20° C. Then, 80 mL of water were added into the reaction solution. The mixture was then stirred, and two phases were separated. The aqueous phase was extracted with dichloromethane (100 mL×2), and the organic phases were combined, dried over anhydrous sodium sulfate, and concentrated under reduced pressure. The resulting residue was purified by silica gel column chromatography with elution system C to obtain the title product 1m (15.7 g, white solid) in a yield of 98%.

MS m/z (ESI): 737.5 [M+1]

Step 11

(S)-2,4-dimethoxybenzyl 2-((2R,3R)-3-((1S,3S,5S)-2-azabicyclo[3.1.0]hexan-3-yl)-3-methoxy-2-methylpropanamido)-3-(2-fluorophenyl)propanoate Condition 1:

Compound 1m (3.9 g, 5.29 mmol) was dissolved in 20 mL of dichloromethane, then diethylamine was added, and stirred for 2 hours at 20° C. Most of the diethylamine was evaporated under reduced pressure. Then, 10 mL of toluene were added, and the mixture was concentrated under reduced pressure and dried. The resulting residue was dissolved in 100 mL of dichloromethane, washed with water (100 mL×2) and saturated sodium chloride solution (100 mL) successively, dried over anhydrous sodium sulfate, and filtered. The filtrate was concentrated under reduced pressure, and the residue was purified by silica gel column chromatography with elution system A to obtain the title product 1n (2.31 g, orange solid) in a yield of 84.9%.

Condition 2:

Compound 1m (15.7 g, 21.3 mmol) was dissolved in 100 mL of dichloromethane, then diethylamine (150 mL, 1.5 mmol) was slowly added at 10-15° C., and stirred for 3 hours. The reaction solution was concentrated under reduced pressure, and the resulting residue was purified by silica gel column chromatography with elution system A to obtain the title product 1n (10 g, yellow oil) in a yield of 91.7%.

MS m/z (ESI): 515.4 [M+1]

Step 12

(S)-2,4-dimethoxybenzyl 2-((2R,3R)-3-((1S,3S,5S)-2-((5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oyl)-2-azabicyclo[3.1.0]hexan-3-yl)-3-methoxy-2-methylpropanamido)-3-(2-fluorophenyl)propanoate Condition 1:

Compound 1n (2.15 g, 4.18 mmol) and (5S,8S,11S,12R)-11-((S)-sec-butyl)-1-(9H-(5S,8S,11S,12R)-11-((S)-sec-butyl)-1-(9H-fluoren-9-yl)-5,8-diisopropyl-12-methoxy-4,10-yl)-5,8-diisopropyl-12-methoxy-4,10-dimethyl-3,6,9-trioxo-2-oxa-4,7,10-triazatetradecan-14-oic acid 1o (2.66 g, 4.18 mmol, prepared by a method disclosed in the patent application "WO 2013072813") were dissolved in 36 mL of a mixed solution of dichloromethane and N,N—N,N-dimethylformamide (V:V=5:1), followed by addition of 2-(7-azabenzotriazol)-N,N,N',N'-2-(7-azabenzotriazol)-N,N,N',N'-tetramethyluronium hexafluorophosphate (1.9 g, 5.01 mmol) and N,N-diisopropylethylamine (2.18 mL, 12.54 mmol). The mixture was stirred for 1 hour at 20° C. 100 mL of water were added, and two phases were separated. The organic phase was washed with water (100 mL×2) and saturated sodium chloride solution (100 mL) successively, dried over anhydrous sodium sulfate, and filtered. The filtrate was concentrated under reduced pressure, and residue was purified by silica gel column chromatography with elution system A to obtain the title product 1p (3.55 g, white foamy solid) in a yield of 75.8%.

Condition 2:

Compound 1n (12.41 g, 19.46 mmol) was dissolved in 100 mL of anhydrous acetonitrile, and then 2-(7-azabenzotriazol)-N,N,N',N'-tetramethyluronium hexafluorophosphate (8.8 g, 23.35 mmol) and N,N-diisopropylethylamine (7.6 g, 58.38 mmol) were added in an ice bath and stirred for 10 minutes at 0-5° C. (5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oic acid 1o was added and stirred for 1 hour. Then, 100 mL of water and 100 mL of ethyl acetate were added into the reaction solution, and two phases were separated. The organic phase was washed with 50 mL of water, and the aqueous phase was extracted with ethyl acetate (100 mL×2). The organic phases were combined, dried over anhydrous sodium sulfate, and concentrated under reduced pressure. The residue was purified by silica gel column chromatography with elution system A to obtain the title product 1p (21.7 g, yellow oil) in a crude yield of about 100%. The product was used directly in the next step.

MS m/z (ESI): 1151.6 [M+18]

Step 13

(S)-2,4-dimethoxybenzyl 2-((2R,3R)-3-((1S,3S,5S)-2-((3R,4S,5S)-4-((S)—N,3-dimethyl-2-((S)-3-methyl-2-(methylamino)butanamido)butanamido)-3-methoxy-5-methylheptanoyl)-2-azabicyclo[3.1.0]hexan-3-yl)-3-methoxy-2-methylpropanamido)-3-(2-fluorophenyl)propanoate Condition 1:

Compound 1p (3.86 g, 3.4 mmol) was dissolved in 20 mL of dichloromethane, and then diethylamine (40 mL, 0.39 mmol) was added, and stirred for 2 hours at 20° C. Most of the diethylamine was evaporated under reduced pressure, and 10 mL of toluene were added into the resulting residue, and the mixture was concentrated under reduced pressure and dried. Then, 100 mL of water and 100 mL of dichloromethane were added into the resulting residue and stirred, and two phases were separated. The organic phase was washed with water (100 mL×2) and saturated sodium chloride solution (100 mL) successively, dried over anhydrous sodium sulfate, and filtered. The filtrate was concentrated under reduced pressure, and the residue was purified by silica gel column chromatography with elution system A to obtain the title product 1q (2.73 g, yellow foamy solid) in yield of 87%.

Condition 2:

The crude product 1p (21.7 g, 19.1 mmol) was dissolved in 100 mL of anhydrous dichloromethane, and then diethylamine (150 mL, 1.5 mmol) was added and stirred for 3 hours at 10-15° C. The reaction solution was concentrated under reduced pressure. The residue was purified by silica gel column chromatography with elution system A to obtain the title product 1q (15.4 g, yellow viscous material) in a yield of 89%.

MS m/z (ESI): 912.9 [M+1]

Step 14

(S)-2,4-dimethoxybenzyl 2-((2R,3R)-3-((1S,3S,5S)-2-((3R,4S,5S)-4-((S)-2-((S)-2-(6-(2,5-dioxo-2,5-dihydro-1H-pyrrol-1-yl)-N-methylhexanamido)-3-methylbutanamido-N,3-dimethylbutanamido)-3-methoxy-5-methylheptanoyl)-2-azabicyclo[3.1.0]hexan-3-yl)-3-methoxy-2-methylpropanamido)-3-(2-fluorophenyl)propanoate Condition 1:

Compound 1q (1.22 g, 1.34 mmol) was dissolved in 24 mL of a mixed solution of dichloromethane and N,N-dimethylformamide (V:V=5:1). 6-Maleimidocaproic acid (282 mg, 1.34 mmol), 2-(7-azabenzotriazol)-N,N,N',N'-tetramethyluronium hexafluorophosphate (310 mg, 1.61 mmol) and N,N-diisopropylethylamine (0.7 mL, 4.02 mmol) were added successively and stirred for 1 hour. Then, 50 mL of water were added into the reaction solution, which was then stirred. Two phases were separated, and the organic phase was washed with water (50 mL×2) and saturated sodium chloride solution (50 mL) successively, dried over anhydrous sodium sulfate, and filtered. The filtrate was concentrated under reduced pressure, and the residue was purified by silica gel column chromatography with elution system A to obtain the title product 1r (780 mg, white foamy solid) in a yield of 52.8%.

Condition 2:

6-maleimidocaproic acid (3.8 g, 17.98 mmol) was dissolved in 200 mL of anhydrous acetonitrile. The temperature of the reaction solution was controlled to −5-0° C. in an ice-salt bath. 2-(7-azabenzotriazol)-N,N,N',N'-tetramethyluronium hexafluorophosphate (7.8 g, 20.68 mmol) and N,N-diisopropylethylamine (7.0 g, 53.34 mmol) were slowly added and stirred for 15 minutes. Compound 1q (15.4 g, 17.98 mmol) was added and stirred for 1 hour. Then, 100 mL of water and 100 mL of ethyl acetate were added into the reaction solution, and two phases were separated. The organic phase was washed with 50 mL of water, and the aqueous phase was extracted with ethyl acetate (100 mL×2), and then the organic phases were combined, dried over anhydrous sodium sulfate, and concentrated under reduced pressure. The residue was purified by silica gel column chromatography with elution system A to obtain the title product 1r (12 g, white solid) in a yield of 60%. The product was used directly in the next step.

MS m/z (ESI): 1122.7 [M+18]

Step 15

(S)-2-((2R,3R)-3-((1S,3S,5S)-2-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)-2-azabicyclo[3.1.0]hexan-3-yl)-3-methoxy-2-methylpropanamido)-3-(2-fluorophenyl) propanoic Acid Condition 1:

Compound 1r (1.56 g, 1.41 mmol) was dissolved in a solution of trifluoroacetic acid in dichloromethane (2.5%, 40 mL) and stirred for 20 minutes. Dichloromethane was evaporated under reduced pressure in an ice bath. The resulting residue was dried under reduced pressure, and then dissolved in dichloromethane. The mixture was wet loaded and purified by silica gel column chromatography with elution system A to obtain the title product 1 (960 mg, white foamy solid) in a yield of 71.1%.

Condition 2:

The crude product 1r (12 g, 10.86 mmol) was dissolved in 50 mL of anhydrous dichloromethane. A solution of trifluoroacetic acid in dichloromethane (2.5%, 150 mL) was added an ice bath and stirred for 3 hours. The reaction solution was concentrated under reduced pressure at low temperature, and the residue was purified by silica gel column chromatography with elution system A to obtain the title product 1 (5.5 g, white solid) in a yield of 53.4%.

MS m/z (ESI): 956.0 [M+1]

$^1$H NMR (400 MHz, CD$_3$OD): δ 7.36-7.30 (m, 1H), 7.29-7.21 (m, 1H), 7.17-7.02 (m, 2H), 6.83-6.79 (m, 2H), 4.81-4.71 (m, 2H), 4.69-4.55 (m, 2H), 4.25-4.15 (m, 1H), 4.13-4.04 (m, 1H), 3.96-3.85 (m, 2H), 3.70-3.61 (m, 1H), 3.55-3.46 (m, 3H), 3.40-3.21 (m, 4H), 3.18-3.10 (m, 2H), 3.07-2.96 (m, 4H), 2.67-2.56 (m, 2H), 2.54-2.34 (m, 3H), 2.29-2.17 (m, 2H), 2.10-1.99 (m, 1H), 1.89-1.57 (m, 7H), 1.52-1.28 (m, 6H), 1.21-1.11 (m, 4H), 1.07-0.96 (m, 6H), 0.95-0.81 (m, 12H), 0.80-0.69 (m, 1H).

Method Disclosed in WO2016/127790 by the Inventors for Synthesizing the Compound of Example 1

(S)-2-((2R,3R)-3-((1S,3S,5S)-2-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)-2-azabicyclo[3.1.0]hexan-3-yl)-3-methoxy-2-methylpropanamido)-3-(2-fluorophenyl) propanoic Acid

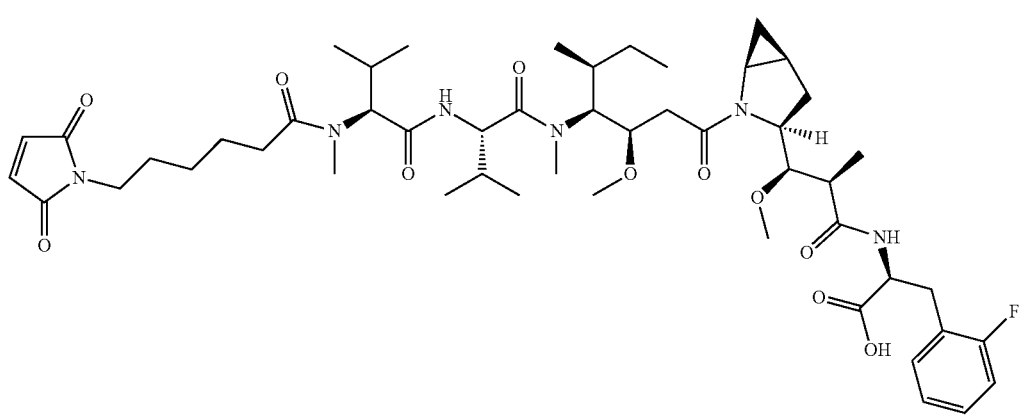

-continued
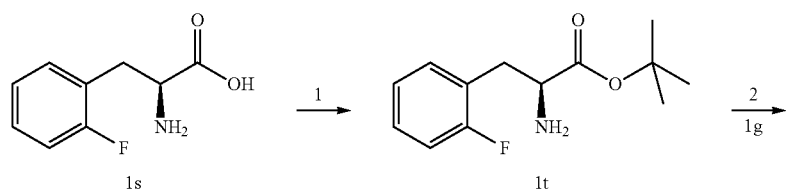
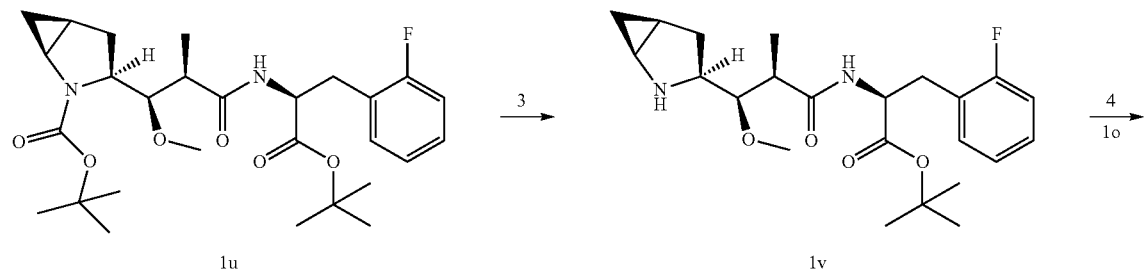
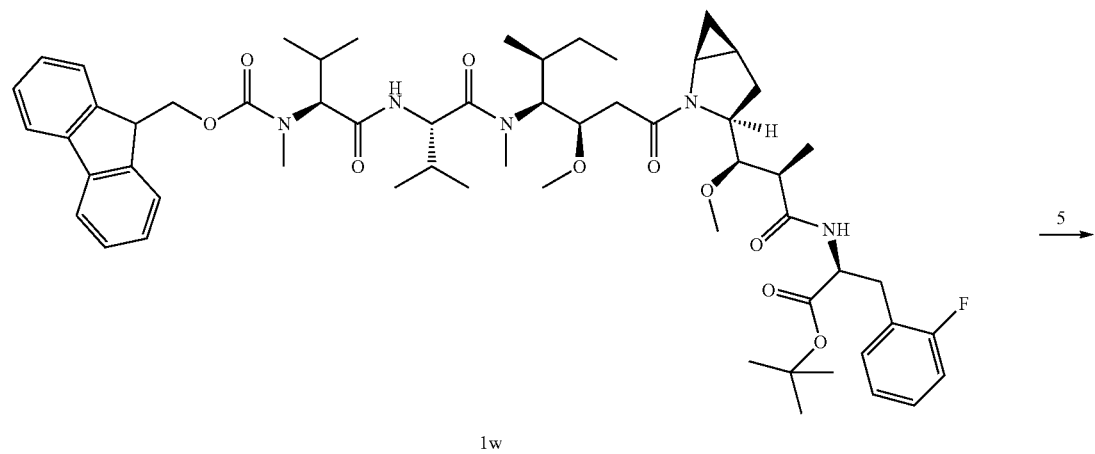
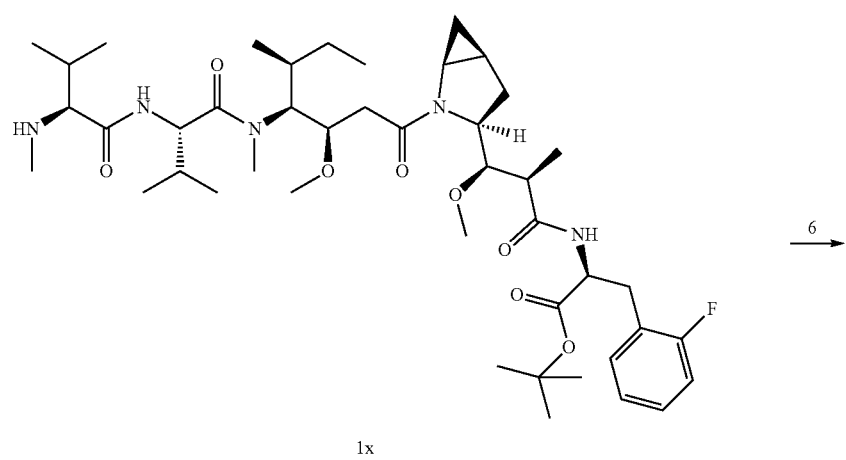

-continued

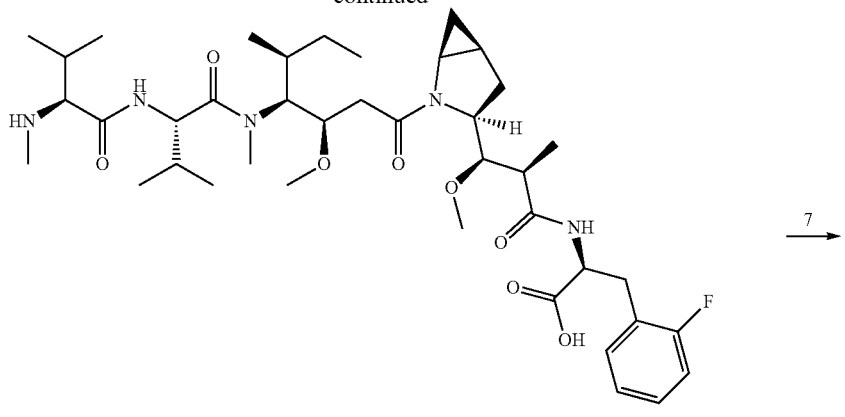

1y

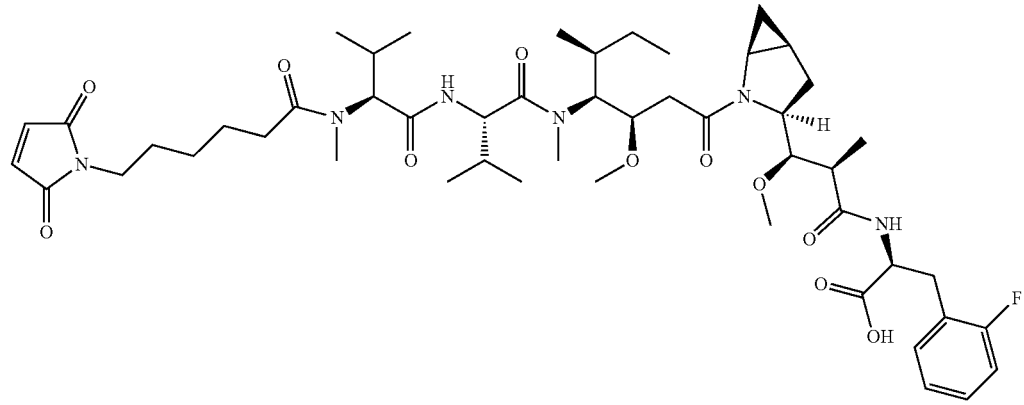

1

Step 1

(S)-tert-butyl 2-amino-3-(2-fluorophenyl)propanoate

The starting material (S)-2-amino-3-(2-fluorophenyl)propanoic acid 1s (400 mg, 2.18 mmol, prepared by a method disclosed in "Advanced Synthesis & Catalysis, 2012, 354 (17), 3327-3332") was dissolved in 10 mL of TBA, and then perchloric acid (300 mg (70%), 3.3 mmol) was added, and stirred for 16 hours at room temperature. After the reaction was completed, 6 mL of water was added, and two phases were separated. The organic phase was washed with saturated sodium bicarbonate solution (5 mL). The aqueous phase was adjusted to pH=8 with saturated sodium bicarbonate solution and extracted with dichloromethane (5 mL×3). The organic phases were combined, washed with water (3 mL) and saturated sodium chloride solution (5 mL) successively, dried over anhydrous sodium sulfate, and filtered. The filtrate was concentrated under reduced pressure to obtain the crude title product (S)-tert-butyl 2-amino-3-(2-fluorophenyl)propanoate 1t (390 mg, yellow oil). The product was used directly in the next step without further purification.

Step 2

(1S,3S,5S)-tert-butyl 3-((1R,2R)-3-(((S)-1-(tert-butoxy)-3-(2-fluorophenyl)-1-oxopropan-2-yl)amino)-1-methoxy-2-methyl-3-oxopropyl)-2-azabicyclo[3.1.0]hexane-2-carboxylate The starting material (2R,3R)-3-((1S,3S,5S)-2-(tert-butoxycarbonyl)-2-(2R,3R)-3-((1S,3S,5S)-2-(tert-butoxycarbonyl)-2-azabicyclo[3.1.0]hexan-3-yl)-3-methoxy-2-propanoic acid 1g (100 mg, 0.334 mmol) was dissolved in 6 mL of a mixed solvent of dichloromethane and dimethylformamide (V/V=5:1), and then the crude product (S)-tert-butyl 2-2-amino-3-(2-fluorophenyl)propanoate 1t (80 mg, 0.334 mmol) was added, followed by addition of N,N-diisopropylethylamine (0.29 mL, 1.67 mmol) and 2-(7-azabenzotriazol)-N,N,N',N'-2-(7-azabenzotriazol)-N,N,N',N'-tetramethyluronium hexafluorophosphate (152.3 mg, 0.40 mmol). The reaction system was stirred at room temperature for 1 hour under an argon atmosphere. After reaction was completed, 10 mL of water were added and stirred, and two phases were separated. The dichloromethane phase was washed with saturated sodium chloride solution (10 mL) solution, dried over anhydrous sodium sulfate, and filtered. The filtrate was concentrated under reduced pressure, the resulting residue was purified by silica gel column chromatography with elution system B to obtain the title product (1S,3S,5S)-tert-butyl 3-((1R,2R)-3-(((S)-1-(tert-butoxy)-3-(2-fluorophenyl)-1-oxopropan-2-yl)amino)-1-methoxy-2- methyl-3-oxopropyl)-2-azabicyclo[3.1.0]hexane-2-carboxylate 1u (173 mg, colorless liquid) in a yield of 99.5%.

MS m/z (ESI): 521.2 [M+1]

Step 3

(S)-tert-butyl 2-((2R,3R)-3-((1S,3S,5S)-2-azabicyclo [3.1.0]hexan-3-yl)-3-methoxy-2-methylpropanamido)-3-(2-fluorophenyl)propanoate The starting material (1S,3S,5S)-tert-butyl 3-((1R,2R)-3-(((S)-1-(tert-butoxy)-3-(2-3-(2-fluorophenyl)-1-oxopropan-2-yl)amino)-1-methoxy-2-methyl-3-oxopropyl)-2-]hexane-2-carboxylate 1u (173 mg, 0.33 mmol) was dissolved in 2 mL of 1,4-dioxane, and then a M solution of hydrogen chloride in dioxane (0.21 mL, 1.16 mmol) was added. The mixture was for 1 hour at room temperature under an argon atmosphere, and then placed in a refrigerator for 12 hours at 0° C. After the reaction was completed, the reaction solution was concentrated under pressure, added with 5 mL dichloromethane and then 10 mL saturated sodium bicarbonate solution, and stirred for 10 minutes, and then two phases were separated. The aqueous phase was extracted dichloromethane (5 mL×3). The dichloromethane phases were combined, washed with saturated sodium chloride solution (10 mL), dried over anhydrous sodium sulfate, and filtered. The filtrate concentrated under reduced pressure to obtain the crude title product (S)-tert-butyl 2-((2R,3R)-3-2-((2R,3R)-3-((1S,3S,5S)-2-azabicyclo[3.1.0]hexan-3-yl)-3-methoxy-2-methylpropanamido)-3-(2-yl)-3-methoxy-2-methylpropanamido)-3-(2-fluorophenyl)propanoate 1v (77 mg, yellow liquid). The product was used directly in the next step without further purification.

MS m/z (ESI): 421.2 [M+1]

Step 4

(S)-tert-butyl 2-((2R,3R)-3-((1S,3S,5S)-2-((5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oyl)-2-azabicyclo[3.1.0]hexan-3-yl)-3-methoxy-2-methylpropanamido)-3-(2-fluorophenyl)propanoate The crude product (S)-tert-butyl 2-((2R,3R)-3-((1S,3S,5S)-2-azabicyclo[3.1.0]hexan-3-yl)-3-methoxy-2-methylpropanamido)-3-(2-fluorophenyl)propanoate 1v (77 mg, 0.183 mmol), and (5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oic acid 1o (116.8 mg, 0.183 mmol) were dissolved in 6 mL of a mixed solvent of dichloromethane and dimethylformamide (V/V=5:1), then N,N-diisopropylethylamine (0.16 mL, 0.915 mmol) and 2-(7-azabenzotriazol)-N,N,N',N'-tetramethyluronium hexafluorophosphate (84 mg, 0.22 mmol) were added. The reaction system was stirred for 1 hour at room temperature under an argon atmosphere. After the reaction was completed, 10 mL of water was added and stirred, and two phases were separated. The dichloromethane phase was washed with saturated sodium chloride solution (10 mL), dried over anhydrous sodium sulfate, and filtered. The filtrate was concentrated under reduced pressure, and the residue was purified by silica gel column chromatography with elution system B to obtain the title product (S)-tert-butyl 2-((2R,3R)-3-((1S,3S,5S)-2-((5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oyl)-2-azabicyclo[3.1.0]hexan-3-yl)-3-methoxy-2-methylpropanamido)-3-(2-fluorophenyl)propanoate 1w (190.5 mg, yellow viscous material) in a yield of 100%.

MS m/z (ESI): 1040.6 [M+1]

Step 5

(S)-tert-butyl 2-((2R,3R)-3-((1S,3S,5S)-2-((3R,4S,5S)-4-((S)—N,3-dimethyl-2-((S)-3-methyl-2-(methylamino)butanamido)butanamido)-3-methoxy-5-methylheptanoyl)-2-azabicyclo[3.1.0]hexan-3-yl)-3-methoxy-2-methylpropanamido)-3-(2-fluorophenyl) propanoate The starting material (S)-tert-butyl 2-((2R,3R)-3-((1S,3S,5S)-2-((5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oyl)-2-azabicyclo[3.1.0]hexan-3-yl)-3-methoxy-2-methylpropanamido)-3-(2-fluorophenyl)propanoate 1w (190.5 mg, 0.183 mmol) was dissolved in 1.5 mL of dichloromethane, then 2 mL of diethylamine were added. The reaction system was stirred for 3 hours at room temperature under an argon atmosphere. After the reaction was completed, the reaction solution was concentrated under reduced pressure to obtain the crude title product (S)-tert-butyl 2-((2R,3R)-3-((1S,3S,5S)-2-((3R,4S,5S)-4-((S)—N,3-dimethyl-2-((S)-3-methyl-2-(methylamino)butanamido)butanamido)-3-methoxy-5-methylheptanoyl)-2-azabicyclo[3.1.0]hexan-3-yl)-3-methoxy-2-methylpropanamido)-3-(2-fluorophenyl)propanoate 1x (150 mg, yellow viscous material). The product was used directly in the next step without further purification.

MS m/z (ESI): 818.5 [M+1]

Step 6

(S)-2-((2R,3R)-3-((1S,3S,5S)-2-((3R,4S,5S)-4-((S)—N,3-dimethyl-2-((S)-3-methyl-2-(methylamino)butanamido)butanamido)-3-methoxy-5-methylheptanoyl)-2-azabicyclo[3.1.0]hexan-3-yl)-3-methoxy-2-methylpropanamido)-3-(2-fluorophenyl) propanoic Acid The crude product (S)-tert-butyl 2-((2R,3R)-3-((1S,3S,5S)-2-((3R,4S,5S)-4-((S)—N,3-2-((2R,3R)-3-((1S,3S,5S)-2-((3R,4S,5S)-4-((S)—N,3-dimethyl-2-((S)-3-methyl-2-amido)butanamido)-3-methoxy-5-methylheptanoyl)-2-azabicyclo[3.1.0]hexan-3-yl)-3-methoxy-2-ethylpropanamido)-3-(2-fluorophenyl)propanoate 1x (150 mg, 0.183 mmol) was dissolved in 1 mL 1,4-dioxane, then 3 mL of a 5.6 M solution of hydrogen chloride in dioxane was added. The mixture was stirred for 12 hours at room temperature under an argon atmosphere. After the reaction was completed, the reaction solution was concentrated under reduced pressure, and the residual solvent was rotary evaporated with diethyl ether. The resulting residue was purified by high performance liquid chromatography to obtain the title product (S)-2-((2R,3R)-3-((1S,3S,5S)-2-((3R,4S,5S)-4-((S)-(S)-2-((2R,3R)-3-((1S,3S,5S)-2-((3R,4S,5S)-4-((S)—N,3-dimethyl-2-((S)-3-methyl-2-tanamido)butanamido)-3-methoxy-5-methylheptanoyl)-2-azabicyclo[3.1.0]hexan-3-yl)-3-methoxy-1-methylpropanamido)-3-(2-fluorophenyl) propanoic acid 1y (28 mg, white powder solid) in a yield of 20%.

MS m/z (ESI): 762.7 [M+1]

$^1$H NMR (400 MHz, CD$_3$OD): δ 7.38-7.18 (m, 2H), 7.13-7.01 (m, 2H), 4.80-4.67 (m, 2H), 4.30-4.15 (m, 1H), 4.13-4.01 (m, 1H), 3.96-3.83 (m, 2H), 3.75-3.60 (m, 2H), 3.42-3.11 (m, 9H), 3.06-2.95 (m, 1H), 2.70-2.58 (m, 4H), 2.28-2.01 (m, 4H), 1.88-1.70 (m, 3H), 1.57-1.25 (m, 4H), 1.22-0.95 (m, 18H), 0.92-0.80 (m, 4H), 0.78-0.65 (m, 1H).

Step 7

The starting material (S)-2-((2R,3R)-3-((1S,3S,5S)-2-((3R,4S,5S)-4-((S)—N,3-dimethyl-2-((S)-3-methyl-2-(methylamino)butanamido)butanamido)-3-methoxy-5-methylheptanoyl)-2-azabicyclo[3.1.0]hexan-3-yl)-3-methoxy-2-methylpropanamido)-3-(2-fluorophenyl) propanoic acid 1y (25 mg, 0.033 mmol) was dissolved in 3 mL of dichloromethane, and then N,N-diisopropylethylamine (0.029 mL, 0.164 mmol) was added. A preformed solution of 6-(2,5-dioxo-2,5-dihydro-1H-pyrrol-1-yl) hexanoyl chloride (11.3 mg, 0.049 mmol) in dichloromethane was added dropwise to the reaction system under an argon atmosphere in an ice bath, and stirred at room temperature for 3 hours. After the reaction was completed, 5 mL of water was added and stirred for 20 minutes, and two phases were separated. The organic phase was dried over anhydrous sodium sulfate, and filtered. The filtrate was concentrated under reduced pressure, and the residue was purified by high performance liquid chromatography to obtain the title product. (S)-2-((2R,3R)-3-((1S,3S,5S)-2-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)-2-azabicyclo[3.1.0]hexan-3-yl)-3-methoxy-2-methylpropanamido)-3-(2-fluorophenyl)propanoic acid 1 (7 mg, yellow viscous material) in a yield of 22.4%.

MS m/z (ESI): 955.4 [M+1]

$^1$H NMR (400 MHz, CD$_3$OD): δ 7.36-7.30 (m, 1H), 7.29-7.21 (m, 1H), 7.17-7.02 (m, 2H), 6.83-6.79 (m, 2H), 4.81-4.71 (m, 2H), 4.69-4.55 (m, 2H), 4.25-4.15 (m, 1H), 4.13-4.04 (m, 1H), 3.96-3.96-3.85 (m, 2H), 3.70-3.61 (m, 1H), 3.55-3.46 (m, 3H), 3.40-3.21 (m, 4H), 3.18-3.10 (m, 2H), 3.07-3.07-2.96 (m, 4H), 2.67-2.56 (m, 2H), 2.54-2.34 (m, 3H), 2.29-2.17 (m, 2H), 2.10-1.99 (m, 1H), 1.89-1.89-1.57 (m, 7H), 1.52-1.28 (m, 6H), 1.21-1.11 (m, 4H), 1.07-0.96 (m, 6H), 0.95-0.81 (m, 12H), 0.80-0.80-0.69 (m, 1H).

The specific steps for preparing the substrate compound of the present invention using the prior art preparation method have been described in WO2016/127790 by the inventors as follows:

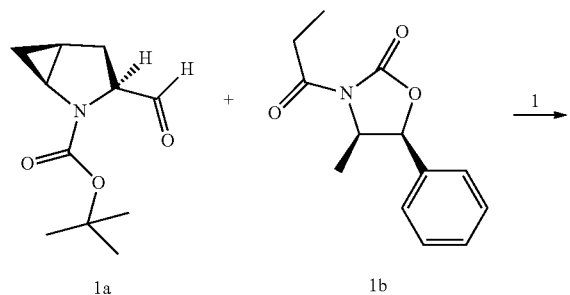

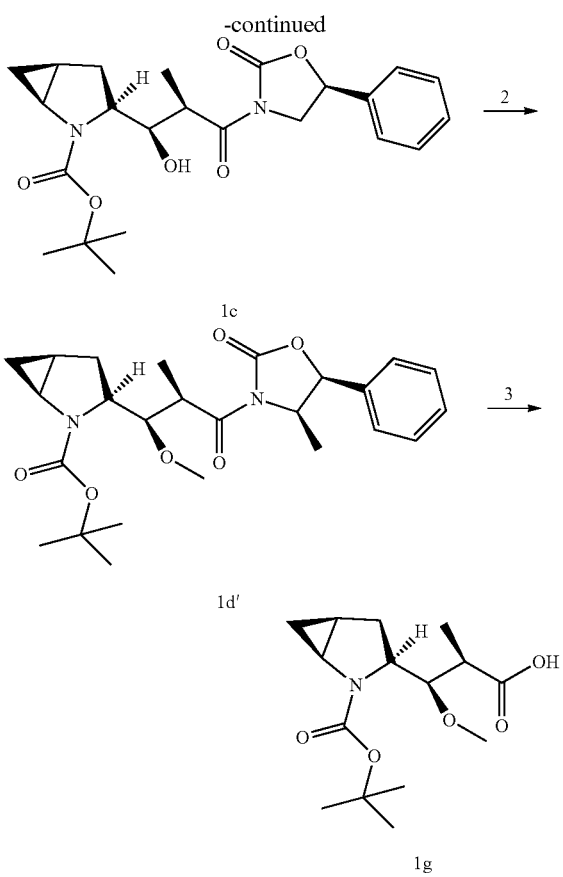

Step 1

(1S,3S,5S)-tert-butyl 3-((1R,2R)-1-hydroxy-2-methyl-3-((4R,5S)-4-methyl-2-oxo-5-phenyloxazolidin-3-yl)-3-oxopropyl)-2-azabicyclo[3.1.0]hexane-2-carboxylate The starting material (4R,5S)-4-methyl-5-phenyl-3-propionyloxazolidin-2-one 1b (1.96 9.26 mmol, prepared by a method disclosed in "Journal of the American Chemical Society, 2003, 125(50), 15512-15520") was dissolved in 25 mL of dichloromethane, and then the mixture was to 0° C. under an argon atmosphere. Triethylamine (1.49 mL, 10.93 mmol) and then dibutylboron trifluoromethanesulfonate (9.7 mL, 9.72 mmol) were added dropwise into the reaction solution at and stirred for 50 minutes at 0° C. The reaction solution was cooled to −75° C. in a dry ice-acetone followed by addition of a solution of (1S,3S,5S)-tert-butyl 3-formyl-2-azabicyclo[3.1.0]hexane-2-3-formyl-2-azabicyclo[3.1.0] hexane-2-carboxylate 1a (2.16 g, 9.26 mmol, prepared by a method disclosed in the patent application "US20100249190") in 7 mL of dichloromethane. The mixture stirred for 1.5 hours at −75° C., stirred for 2 hours at 0° C., and stirred for 1 hour at room temperature. After the reaction was completed, 36 mL of a mixed solution of phosphate buffer (pH=7.0) and methanol (V/V=1:3) was added, followed by addition of 36 mL of a mixed solution of methanol and hydrogen peroxide (30%) (V/V=2:1), and stirred for 1 hour at room temperature. The organic phase was removed by concentration under reduced pressure, then a small amount of water was added. mixture was extracted with diethyl ether (50 mL×3), washed with 5% sodium bicarbonate solution and saturated sodium chloride solution (150 mL) successively, dried over anhydrous sodium sulfate, and filtered. The filtrate was concentrated under reduced pressure, and the residue was purified by silica gel column chromatography with elution system B to obtain the title product (1S,3S,5S)-tert-(1S,3S,5S)-tert-butyl 3-((1R,2R)-1-hydroxy-2-methyl-3-((4R,5S)-4-methyl-2-oxo-5-3-((1R,2R)-1-hydroxy-2-methyl-3-((4R,5S)-4-methyl-2-oxo-5-phenyloxazolidin-3-yl)-3-oxopropyl)-2-azabicyclo[3.1.0]hexane-2-carboxylate 1c (2.4 g, white foamy solid) in a yield of 58.5%.

MS m/z (ESI): 345.1 [M–100+1]

Step 2

(1S,3S,5S)-tert-butyl 3-((1R,2R)-1-methoxy-2-methyl-3-((4R,5S)-4-methyl-2-oxo-5-phenyloxazolidin-3-yl)-3-oxopropyl)-2-azabicyclo [3.1.0]hexane-2-carboxylate The starting material (1S,3S,5S)-tert-butyl 3-((1R,2R)-1-hydroxy-2-methyl-3-((4R,5S)-4-methyl-2-oxo-5-phenyloxazolidin-3-yl)-3-oxopropyl)-2-azabicyclo[3.1.0]hexane-2-carboxylate 1c (1.4 g, 3.15 mmol) was dissolved in 20 mL of dichloromethane, and then 1.4 g crushed molecular sieve was added, followed by addition of 1,8-bis(dimethylamino) naphtalene (1.75 g, 8.19 mmol) and trimethyloxonium tetrafluoroborate (1.16 g, 7.87 mmol) at 0° C. under an argon atmosphere. The reaction was protected from light and stirred for 40 hours at room temperature. After the reaction was completed, the mixture was filtered, and the filter cake was washed with dichloromethane. The filtrate was washed with saturated ammonium chloride solution (50 mL×4) to remove excess 1,8-bis(dimethylamino)naphtalene, and then washed with saturated sodium chloride solution (120 mL), dried over anhydrous sodium sulfate, and filtered. The filtrate was concentrated under reduced pressure, and the resulting residue was purified by silica gel column chromatography with elution system B to obtain the title product (1S,3S,5S)-tert-butyl 3-((1R,2R)-1-methoxy-2-methyl-3-((4R,5S)-4-methyl-2-oxo-5-phenyloxazolidin-3-yl)-3-oxopropyl)-2-azabicyclo[3.1.0]hexane-2-carboxylate 1d' (400 mg, white solid) in a yield of 27.8%.

MS m/z (ESI): 459.4 [M+1]

Step 3

(2R,3R)-3-((1S,3S,5S)-2-(tert-butoxycarbonyl)-2-azabicyclo[3.1.0]hexan-3-yl)-3-methoxy-2-methylpropanoic Acid The starting material (1S,3S,5S)-tert-butyl 3-((1R,2R)-1-methoxy-2-methyl-3-((4R,5S)-4-methyl-2-oxo-5-phenyloxazolidin-3-yl)-3-oxopropyl)-2-azabicyclo[3.1.0]hexane-2-carboxylate 1d' (400 mg, 0.87 mmol) was dissolved in 24 mL of tetrahydrofuran and cooled to 0° C. under an argon atmosphere. Then, 30% hydrogen peroxide (0.34 mL/0.38 g, 3.31 mmol) was added dropwise and slowly, followed by addition of lithium hydroxide monohydrate (62 mg, 1.48 mmol). The reaction system was stirred for 20 hours at room temperature. After the reaction was completed, sodium sulfite solid (440 mg, 3.48 mmol) was added to the reaction solution and stirred for 1 hour at room temperature. Then, 10 mL of water were added, and the organic phase was removed by concentration under reduced pressure. The resulting residue was extracted with dichloromethane (40 mL×2). The aqueous phase was added with 2N hydrogen chloride until the pH of the reaction solution was 3-4. The mixture was extracted with ethyl acetate (25 mL×3). The ethyl acetate phase was washed with water (50 mL) and saturated sodium chloride solution (50 mL) successively, dried over anhydrous sodium sulfate and filtered. The filtrate was concentrated under reduced pressure to obtain the title product (2R,3R)-3-((1S,3S,5S)-2-(tert-butoxycarbonyl)-2-azabicyclo[3.1.0]hexan-3-yl)-3-methoxy-2-methylpropanoic acid 1g (230 mg, colorless liquid) in a yield of 88.0%.

MS m/z (ESI): 200.1 [M–100+1]

The yields of intermediate 1g prepared by the two methods are compared and shown in the following table:

| | Yield of step 1 | Yield of step 2 | Yield of step 3 | Yield of step 4 | Yield of step 5 | Total yield |
|---|---|---|---|---|---|---|
| Synthesis method of WO2016/127790 | 58.5% | 27.8% | 88.0% | | | 14.3% |
| Synthesis method of the present invention | 72.3% | 92% | 84.2% | 87.2% | 100% | 48.8% |

It can be seen from the above table:

The method of the present invention firstly protects the carboxyl group and then adds methyl group. Although the synthesis route is longer than that of the prior art, the total yield is greatly increased by about 3 times. The method of the present invention has characteristics suitable for industrial production and so on, and has significant social and economic benefits.

Since the present invention has been described in accordance with its specific embodiments, some modifications and equivalents are apparent to the person skilled in the art and are included in the scope of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A compound of formula (III),

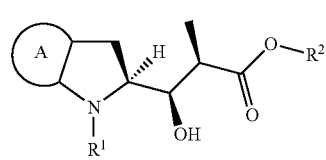

(III)

wherein:
A is a 3 to 8 membered ring;
$R^1$ is hydrogen or an amino protecting group; and
$R^2$ is hydrogen or a carboxyl protecting group.

2. A process for preparing the compound of formula (III) according to claim 1, comprising hydrolyzing a chiral compound of formula (II) comprising a chiral auxiliary group ($R^3$) under an alkaline condition and optionally adding a carboxyl protecting group to obtain the compound of formula (III),

55

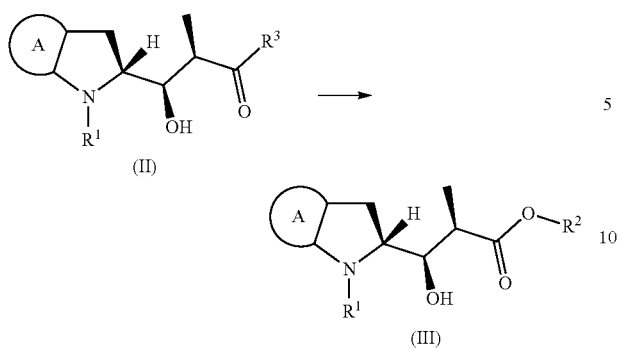

wherein:
the chiral auxiliary group (R³) is selected from the group consisting of:

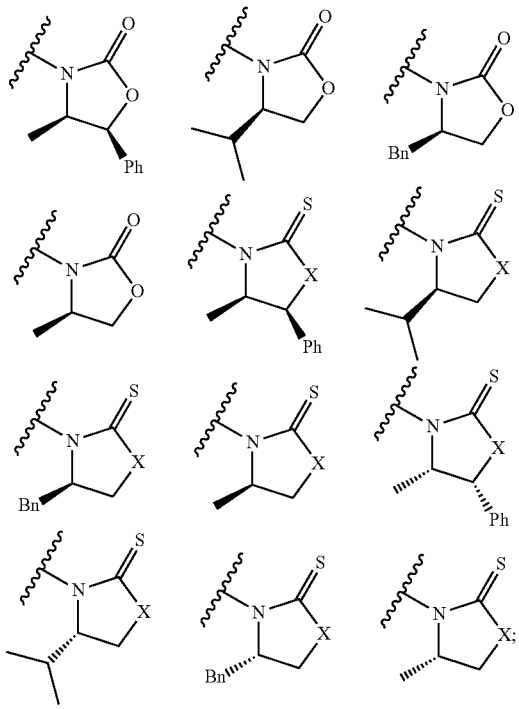

X is sulfur or oxygen;
alkaline reagent is selected from the group consisting of sodium hydroxide, potassium hydroxide, sodium hydride, sodium carbonate, sodium bicarbonate, potassium carbonate, potassium bicarbonate, cesium carbonate and lithium hydroxide; and
R¹ to R² are as defined in formula (III) above.

3. A compound of formula (IV),

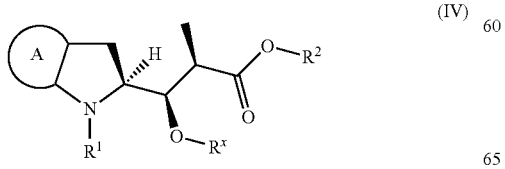

56 wherein:
A is a 3 to 8 membered ring;
R¹ is hydrogen or an amino protecting group;
R² is a carboxyl protecting group; and
R$^x$ is selected from the group consisting of alkyl and cycloalkyl, wherein the alkyl and cycloalkyl are each independently and optionally substituted by one or more groups selected from the group consisting of alkyl, haloalkyl, halogen, hydroxy, amino, nitro, cyano, alkoxy, hydroxyalkyl, cycloalkyl, heterocyclyl, aryl and heteroaryl.

4. A process for preparing the compound of formula (IV) according to claim 3, comprising reacting a compound of formula (III) with an alkylating agent to obtain the compound of formula (IV),

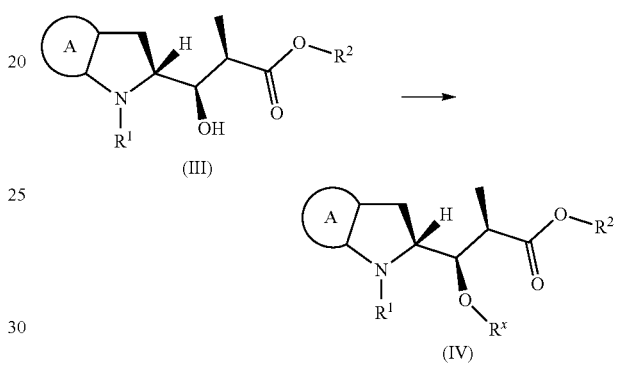

wherein:
the alkylating agent is selected from the group consisting of alkyl halide, dimethyl sulfate, dimethyl carbonate, sulfonate, trimethyl phosphate and Me₃$^+$BF₄$^-$; and
A, R¹, R² and R$^x$ are as defined in formula (IV) above.

5. A process for preparing a compound of formula (V) using the compound of formula (IV) according to claim 3, comprising removing the carboxyl protecting group on the compound of formula (IV) to obtain the compound of formula (V),

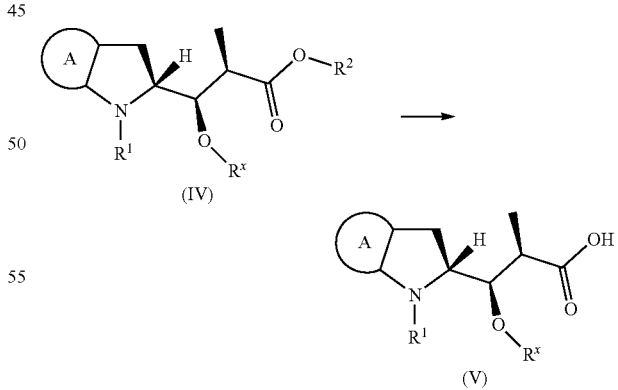

wherein:
A, R¹, R² and R$^x$ are as defined in formula (IV) above.

6. The process for preparing the compound of formula (V) according to claim 5, further comprising preparing the compound of formula (IV) from a compound of formula (III),

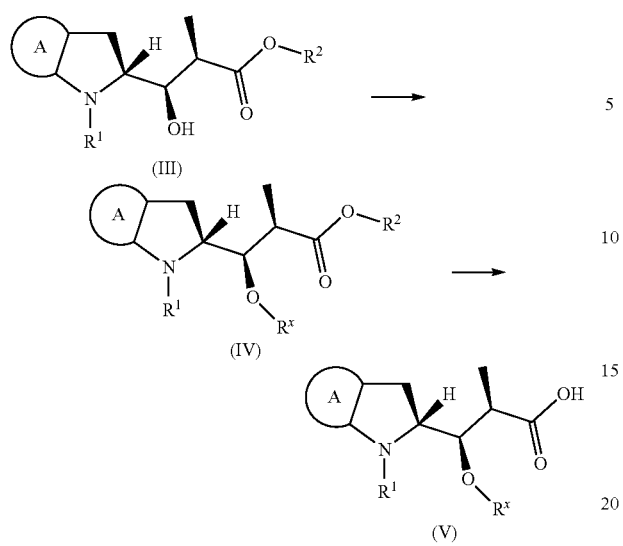
wherein:
A, R¹, R² and $R^x$ are as defined in formula (IV) above.
7. The process for preparing the compound of formula (V) according to claim 6, further comprising preparing a compound of formula (III) from a compound of formula (II),
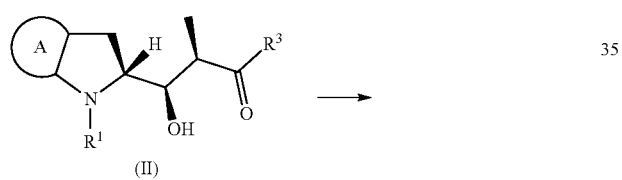
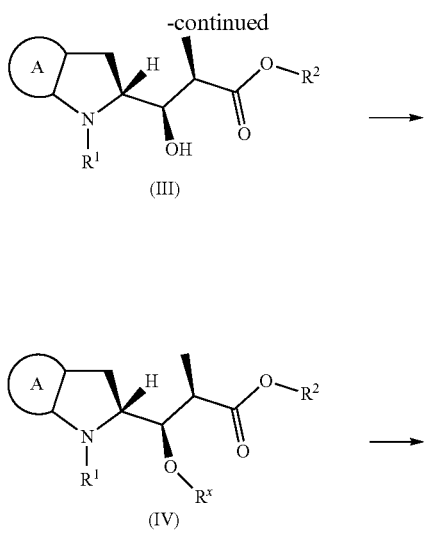
wherein:
A, R¹, R² and $R^x$ are as defined in formula (IV) above.
8. A process for preparing a compound of formula (I),
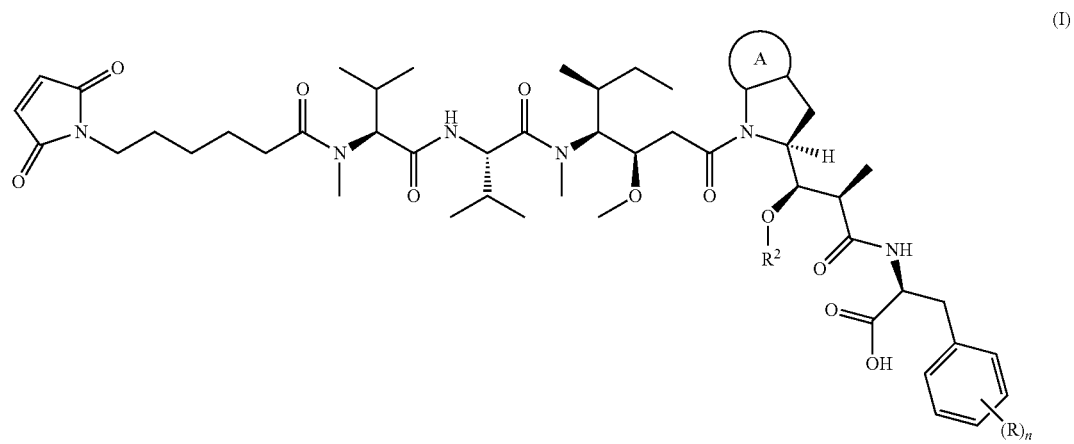

comprising hydrolyzing a chiral compound of formula (II) comprising a chiral auxiliary group $R^3$ under an alkaline condition and optionally adding a carboxyl protecting group to obtain a compound of formula (III); alkylating the compound of formula (III) with an alkylating agent to obtain a compound of formula (IV); removing the carboxyl protecting group on the compound of formula (IV) to obtain a compound of formula (V); and preparing the compound of formula (I) from the compound of formula (V),

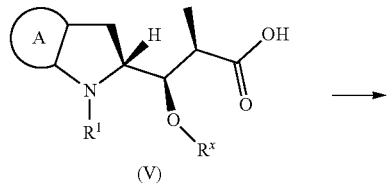

(V)

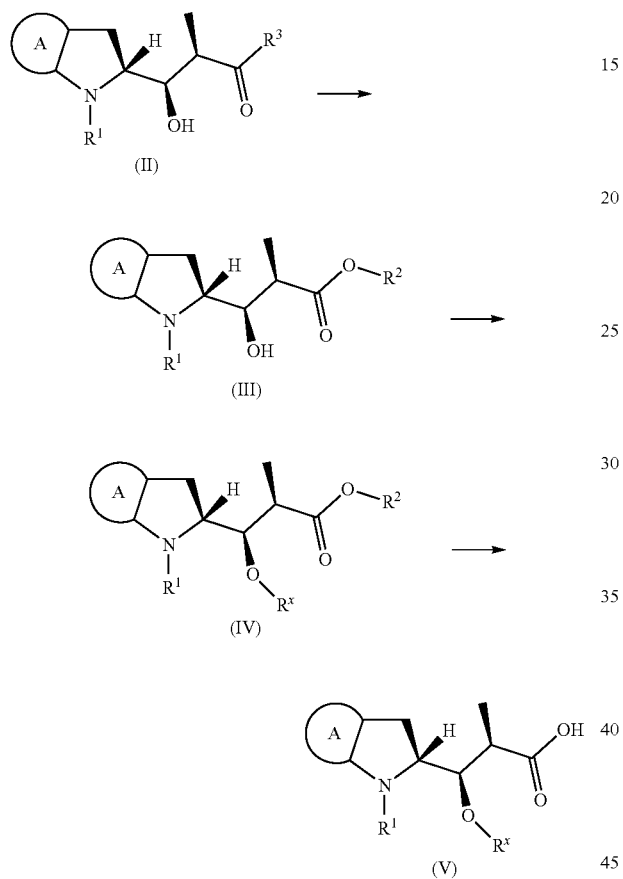

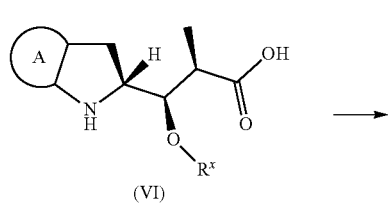

(VI)

wherein:

A, $R^1$ and $R^x$ are as defined in formula (V) above.

10. The process for preparing the compound of formula (I) according to claim 9, further comprising adding a protecting group of Fmoc to the compound of formula (VI) to obtain a compound of formula (VIII),

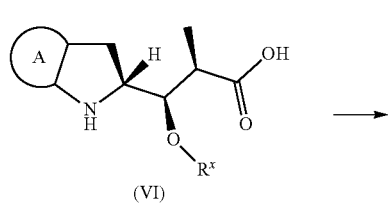

(VI)

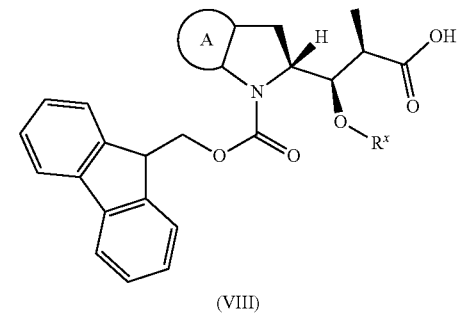

(VIII)

wherein:

A is a 3 to 8 membered ring;

R is halogen;

$R^1$ is an amino protecting group;

$R^2$ is a carboxyl protecting group;

$R^x$ is selected from the group consisting of alkyl and cycloalkyl, wherein the alkyl and cycloalkyl are each independently and optionally substituted by one or more groups selected from the group consisting of alkyl, haloalkyl, halogen, hydroxy, amino, nitro, cyano, alkoxy, hydroxyalkyl, cycloalkyl, heterocyclyl, aryl and heteroaryl; and n is 1, 2, 3, 4 or 5.

9. The process for preparing the compound of formula (I) according to claim 8, further comprising removing the amino protecting group on the compound of formula (V) to obtain a compound of formula (VI), wherein:

A and $R^x$ are as defined in formula (VI) above.

11. The process for preparing the compound of formula (I) according to claim 8, further comprising: adding a carboxyl protecting group to a compound of formula (IX) to obtain a compound of formula (X), and removing the Fmoc on the compound of formula (X) to obtain a compound of formula (XI),

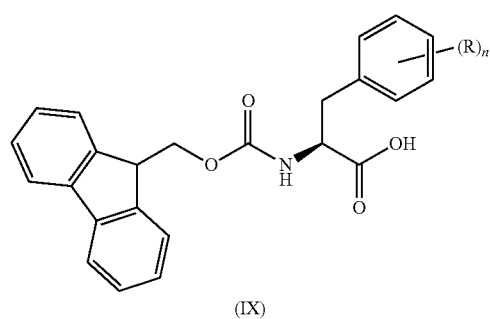
(IX)
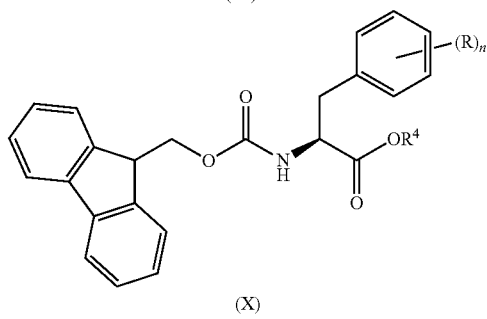
(X)
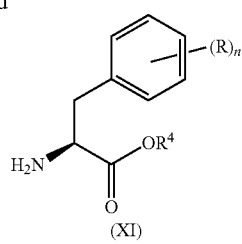
(XI)
wherein:
R[4] is a carboxyl protecting group; and
R and n are as defined in formula (I) above.
12. The process for preparing the compound of formula (I) according to claim 8, further comprising: amidating a compound of formula (VIII) with a compound of formula (XI) in the presence of a condensing agent to obtain a compound of formula (XII),
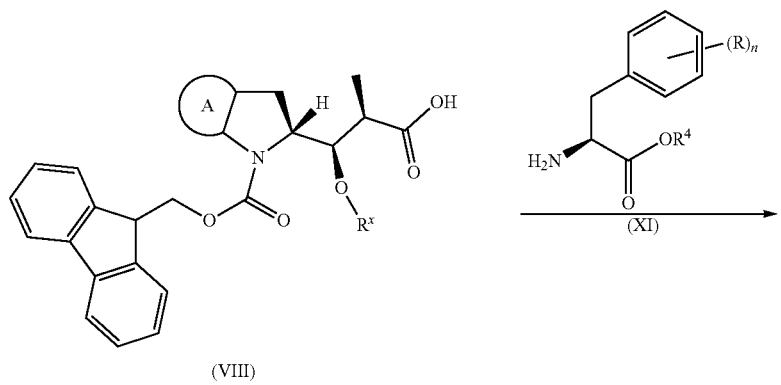
(VIII)
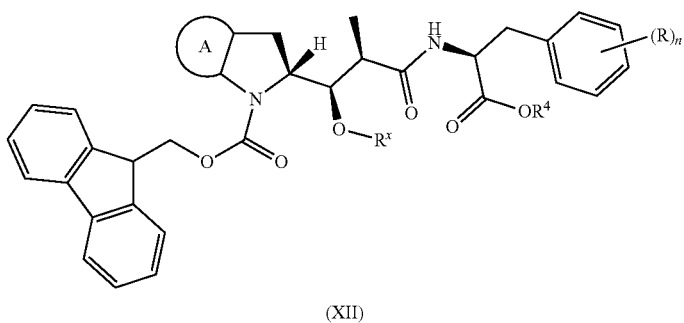
(XII)

wherein:
the condensing agent is selected from the group consisting of 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'-tetramethyluronium hexafluorophosphate, 2-(7-azabenzotriazol)-N,N,N', N'-tetramethyluronium hexafluorophosphate, benzotriazol-1-yloxytris(dimethylamino)-phosphonium hexafluorophosphate and benzotriazole-1-yl-oxytripyrrolidino-phosphonium hexafluorophosphate;

$R^4$ is a carboxyl protecting group; and

A, R, $R^x$ and n are as defined in formula (I) above.

13. The process for preparing the compound of formula (I) according to claim 8, further comprising:

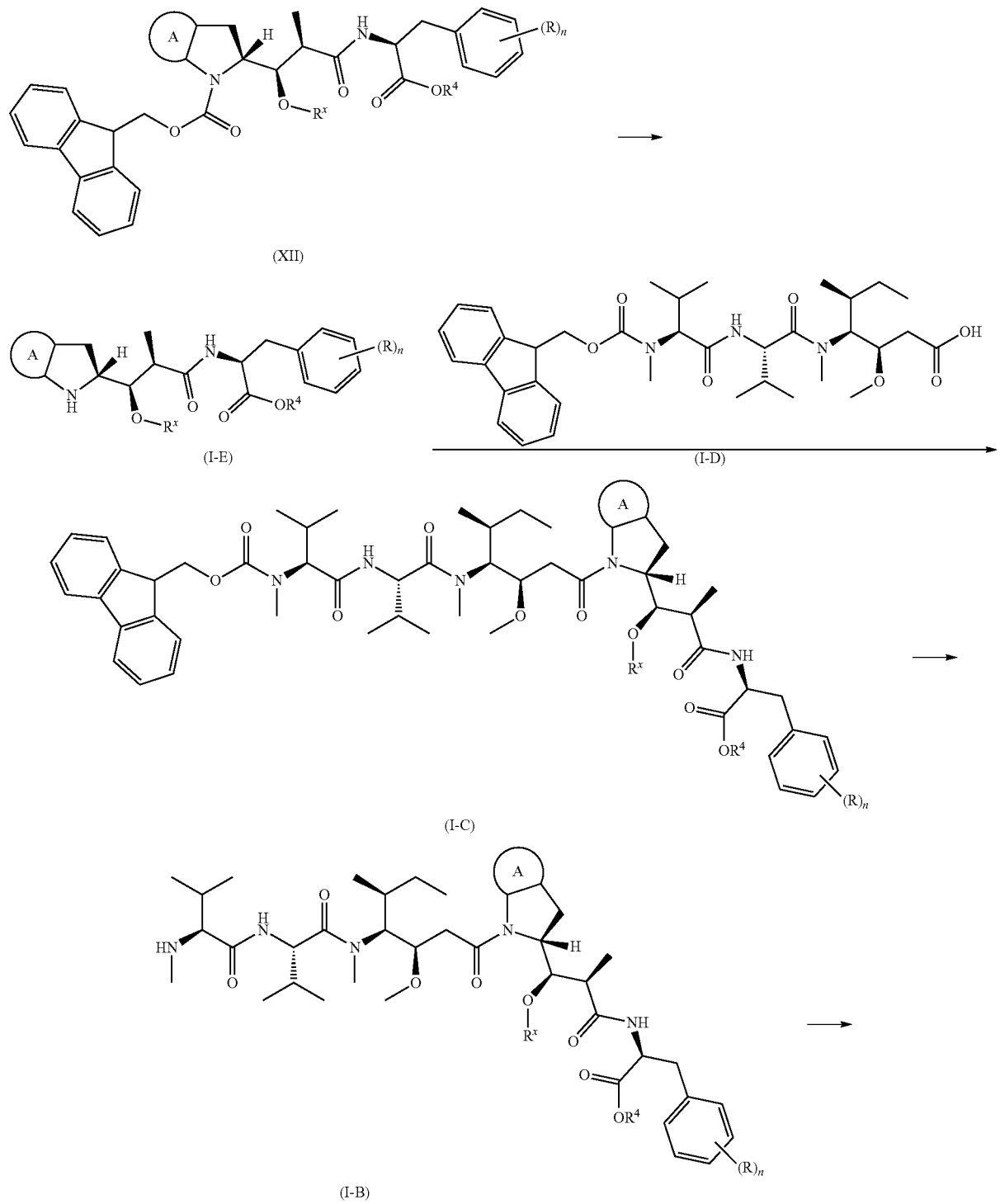

-continued

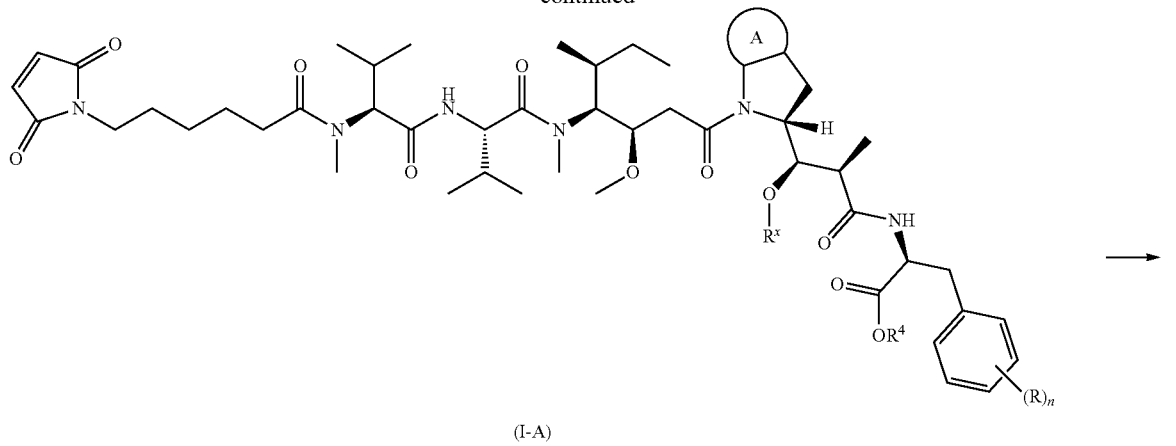

(I-A)

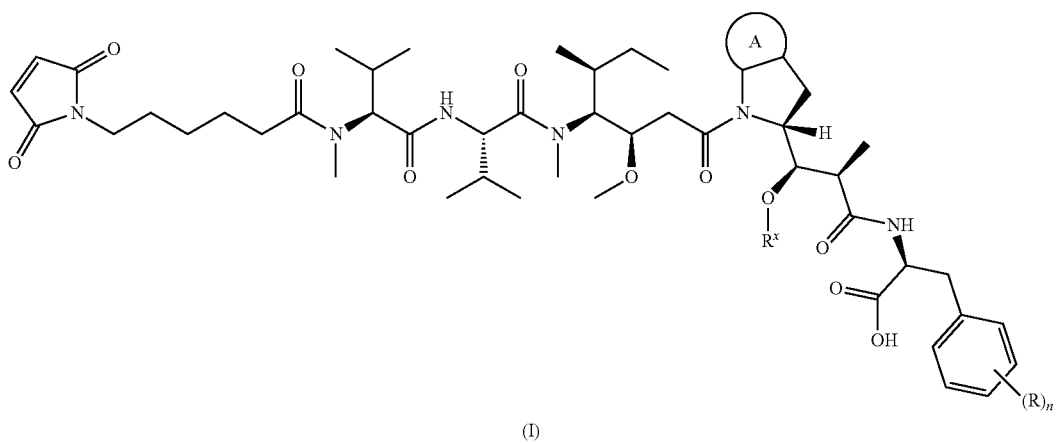

(I)

1) removing the protecting group of Fmoc on a compound of formula (XII) under an alkaline condition to obtain a compound of formula (I-E);
2) amidating the compound of formula (I-E) with a compound of formula (I-D) in the presence of a condensing agent to obtain a chiral intermediate of formula (I-C);
3) removing the protecting group of Fmoc on the compound of formula (I-C) under an alkaline condition to obtain a chiral compound of formula (I-B);
4) amidating the compound of formula (I-B) with 6-maleimidocaproic acid in the presence of a condensing agent to obtain a compound of formula (I-A);
5) removing the carboxyl protecting group on compound of formula (I-A) under an acidic condition to obtain the target compound of formula (I);

wherein:

$R^4$ is a carboxyl protecting group;

the reagent that provides an alkaline condition in step 1) or step 3) comprises an organic base or an inorganic base, wherein the organic base is selected from the group consisting of triethylamine, diethylamine, N,N-diisopropylethylamine, pyridine, sodium bis(trimethylsilyl)amide, n-butyllithium, potassium tert-butoxide and tetrabutylammonium bromide, and the inorganic base is selected from the group consisting of lithium hydroxide, sodium hydroxide, potassium hydroxide, sodium hydride, sodium carbonate, sodium bicarbonate, potassium carbonate, potassium bicarbonate and cesium carbonate;

the condensing agent in step 2) or step 4) is selected from the group consisting of 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'-tetramethyluronium hexafluorophosphate, 2-(7-azabenzotriazol)-N,N,N',N'-tetramethyluronium hexafluorophosphate, benzotriazol-1-(dimethylamino)-phosphonium hexafluorophosphate and benzotriazole-1-yl-oxytripyrrolidino-phosphonium hexafluorophosphate;

the reagent that provides an acidic condition in step 5) is selected from the group consisting of hydrogen chloride solution, hydrochloric acid, nitric acid, phosphoric acid, p-toluenesulfonic acid, $Me_3SiCl$, TMSOTf, trifluoroacetic acid and sulfuric acid; and A, R, $R^x$ and n are as defined in formula (I) above.

14. The process for preparing the compound of formula (I) according to claim 8, further comprising amidating the compound of formula (V) with a compound of formula (XI) in the presence of a condensing agent to obtain a compound of formula (VII),

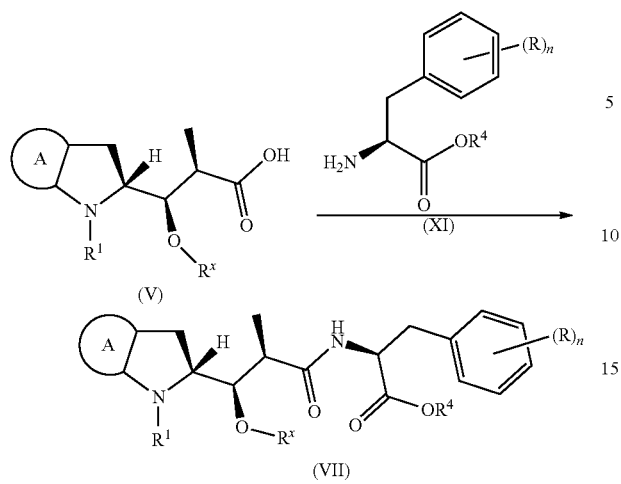

wherein:

the condensing agent is selected from the group consisting of 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'-tetramethyluronium hexafluorophosphate, 2-(7-azabenzotriazol)-N,N,N',N'-tetramethyluronium hexafluorophosphate, benzotriazol-1-yloxytris(dimethylamino)-phosphonium hexafluorophosphate and benzotriazole-1-yl-oxytripyrrolidino-phosphonium hexafluorophosphate;

$R^4$ is a carboxyl protecting group; and

A, R, $R^1$, $R^x$ and n are as defined in formulas (I) and (V) above.

15. The process for preparing the compound of formula (I) according to claim 8, further comprising:

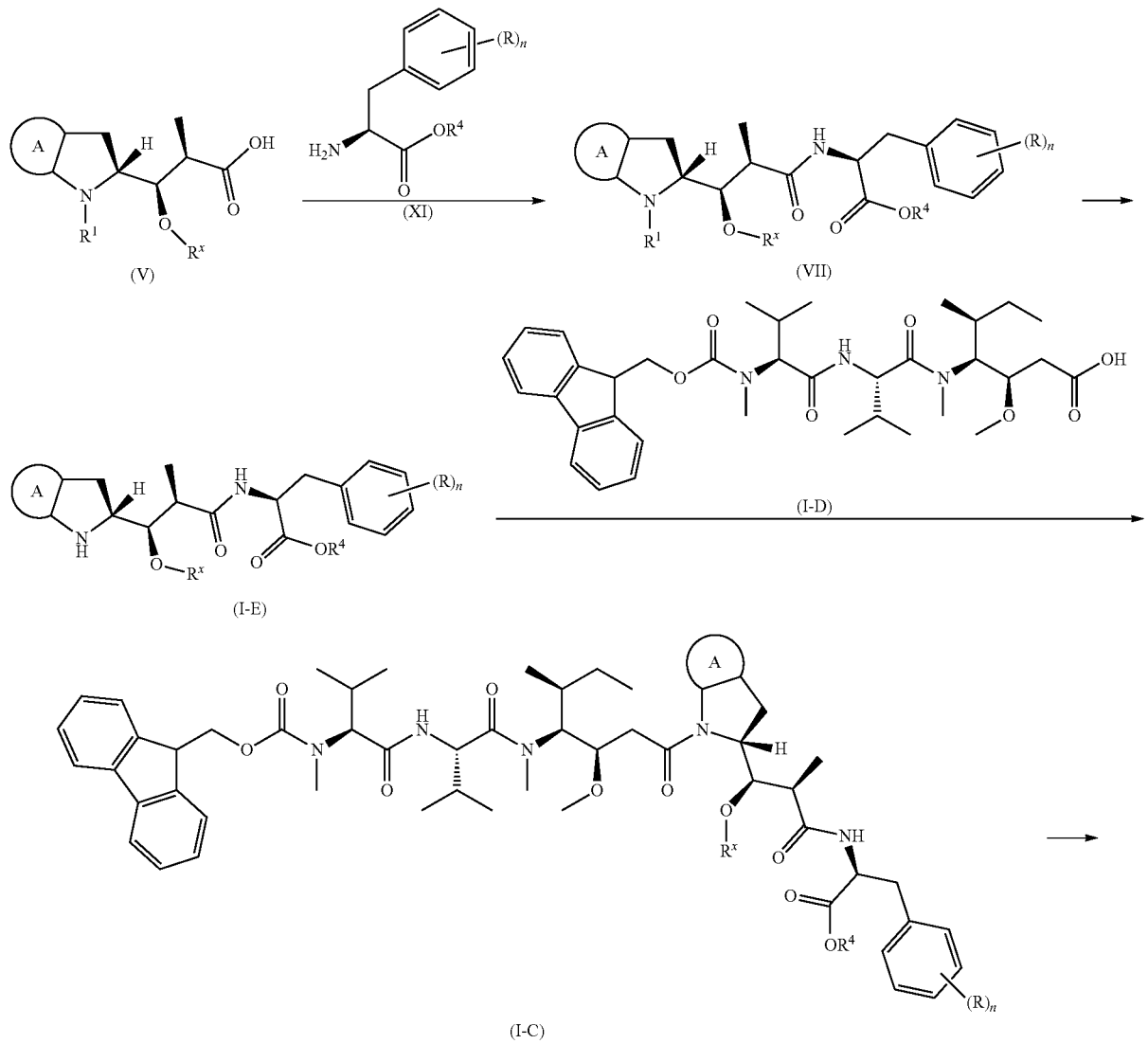

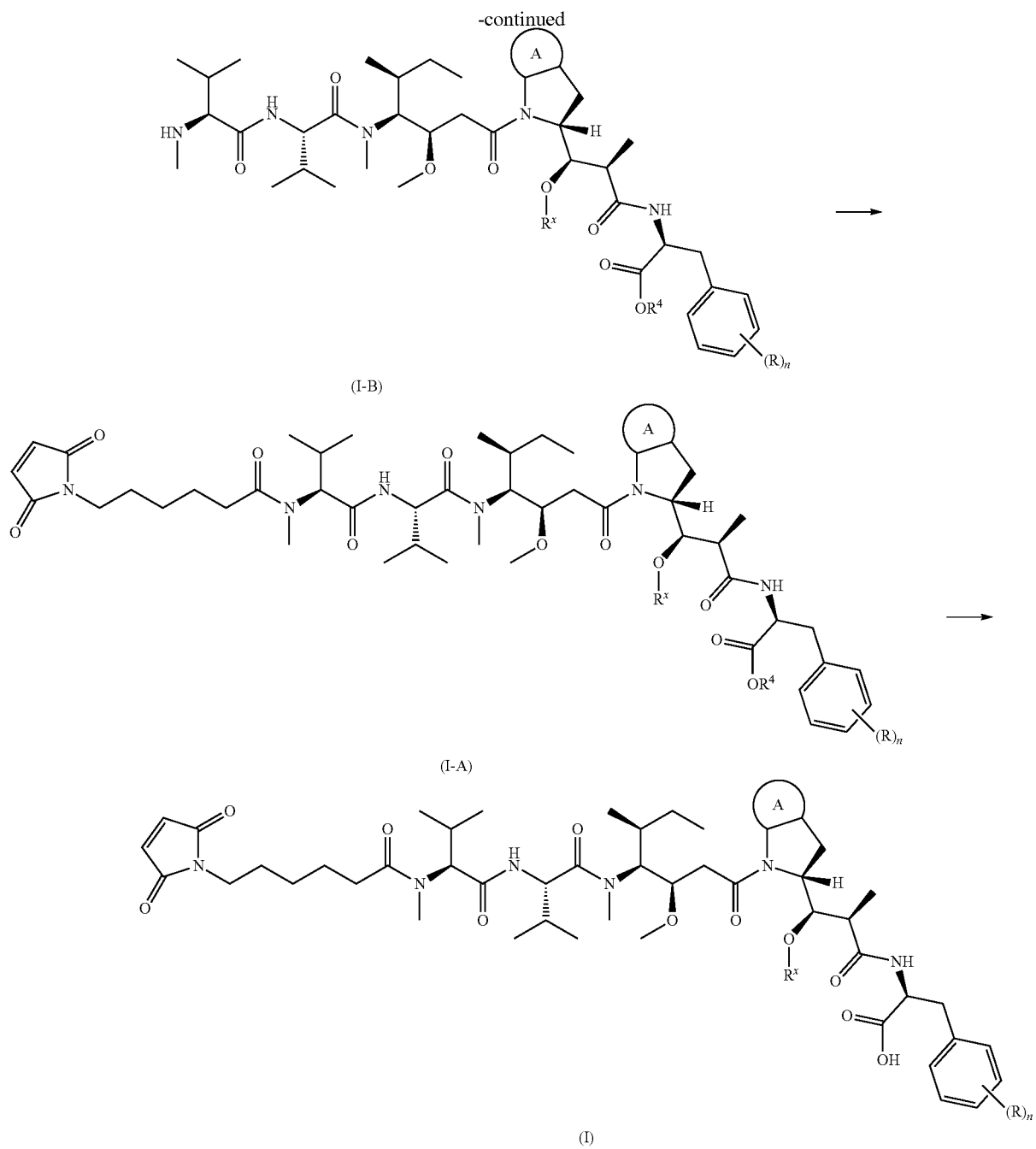

1) amidating the compound of formula (V) with a compound of formula (XI) in the presence of a condensing agent to obtain a compound of formula (VII);
2) removing the amino protecting group on the compound of formula (VII) under an alkaline condition to obtain a compound of formula (I-E);
3) amidating the compound of formula (I-E) with a compound of formula (I-D) in the presence of a condensing agent to obtain a chiral intermediate of formula (I-C);
4) removing the protecting group of Fmoc on the compound of formula (I-C) under an alkaline condition to obtain a chiral compound of formula (I-B);
5) amidating the compound of formula (I-B) with 6-maleimidocaproic acid in the presence of a condensing agent to obtain a compound of formula (I-A);
6) removing the carboxyl protecting group on the compound of formula (I-A) under an acidic condition to obtain the target compound of formula (I);

wherein:
the condensing agent in step 1), step 3), or step 5) is selected from the group consisting of 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azabenzotriazole, O-benzotriazole-N,N,N',N'- tetramethyluronium hexafluorophosphate, 2-(7-azabenzotriazol)-N,N,N',N'-tetramethyluronium hexafluorophosphate, benzotriazol-1-yloxytris(dimethylamino)-phosphonium hexafluorophosphate and benzotriazole-1-yl-oxytripyrrolidino-phosphonium hexafluorophosphate;

the reagent that provides an alkaline condition in step 2) or step 4) comprises an organic base or an inorganic base, wherein the organic base is selected from the group consisting of triethylamine, diethylamine, N,N-diisopropylethylamine, pyridine, sodium bis(trimethylsilyl)amide, n-butyllithium, potassium tert-butoxide and tetrabutylammonium bromide, and the inorganic base is selected from the group consisting of lithium hydroxide, sodium hydroxide, potassium hydroxide, sodium hydride, sodium carbonate, sodium bicarbonate, potassium carbonate, potassium bicarbonate and cesium carbonate;

the reagent that provides an acidic condition in step 6) is selected from the group consisting of hydrogen chloride solution, hydrochloric acid, nitric acid, phosphoric acid, p-toluenesulfonic acid, $Me_3SiCl$, TMSOTf, trifluoroacetic acid and sulfuric acid;

$R^4$ is a carboxyl protecting group; and

A, R, $R^1$, $R^x$ and n are as defined in formulas (I) and (V) above.

16. The process for preparing the compound of formula (I) according to claim 8, wherein R is selected from the group consisting of fluorine, chlorine, bromine and iodine.

17. The process for preparing the compound of formula (I) according to claim 8, wherein $R^1$ is selected from the group consisting of Boc, Fmoc, Alloc, Troc, Teoc, CBz, Tosyl, Nosyl and t-Bu.

18. The process for preparing the compound of formula (I) according to claim 8, wherein $R^2$ is selected from the group consisting of DMB, Bn, Allyl, NP, Me, PMB, MEM and t-Bu.

19. The process for preparing the compound of formula (I) according to claim 8, wherein $R^x$ is methyl.

20. The process for preparing the compound of formula (I) according to claim 8, wherein A is a 3 membered ring.

21. The process for preparing the compound of formula (I) according to claim 8, wherein R is fluorine.

22. The process for preparing the compound of formula (I) according to claim 15, wherein the condensing agent in step 1), step 3), or step 5 is 2-(7-azabenzotriazol)-N,N,N', N'-tetramethyluronium hexafluorophosphate.

23. The process for preparing the compound of formula (I) according to claim 15, wherein the alkaline condition in step 2) or step 4) is provided by the reagent diethylamine.

24. The process for preparing the compound of formula (I) according to claim 15, wherein the acidic condition in step 6) is provided by the reagent trifluoroacetic acid.

25. The process for preparing the compound of formula (I) according to claim 15, wherein $R^4$ is DMB.

26. The process for preparing the compound of formula (IV) according to claim 4, wherein the alkylating agent is methyl iodide or $Me_3^+BF_4^-$.

27. The process for preparing the compound of formula (III) according to claim 2, wherein the alkaline reagent is lithium hydroxide.

* * * * *